(12) United States Patent
Davey et al.

(10) Patent No.: US 10,241,075 B2
(45) Date of Patent: Mar. 26, 2019

(54) METHODS, SYSTEMS, AND COMPUTER READABLE MEDIA FOR NUCLEIC ACID SEQUENCING

(75) Inventors: Melville Davey, Westbrook, CT (US); Simon Cawley, Oakland, CA (US); Alan Williams, Albany, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1145 days.

(21) Appl. No.: 13/340,490

(22) Filed: Dec. 29, 2011

(65) Prior Publication Data
US 2012/0173159 A1 Jul. 5, 2012

Related U.S. Application Data

(60) Provisional application No. 61/428,733, filed on Dec. 30, 2010.

(51) Int. Cl.
G01N 27/414 (2006.01)
G06F 19/22 (2011.01)
G01N 27/27 (2006.01)

(52) U.S. Cl.
CPC .......... *G01N 27/4145* (2013.01); *G06F 19/22* (2013.01); *G01N 27/27* (2013.01)

(58) Field of Classification Search
CPC ........................... G01N 27/4145; G06F 19/22
USPC ........................................................ 702/20
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,210,015 A | 5/1993 | Gelfand et al. |
| 5,399,491 A | 3/1995 | Kacian et al. |
| 5,587,128 A | 12/1996 | Wilding et al. |
| 5,750,341 A | 5/1998 | Macevicz |
| 5,854,033 A | 12/1998 | Lizardi |
| 6,033,546 A | 3/2000 | Ramsey |
| 6,054,034 A | 4/2000 | Soane et al. |
| 6,174,670 B1 | 1/2001 | Wittwer et al. |
| 6,210,891 B1 | 4/2001 | Nyren et al. |
| 6,258,568 B1 | 7/2001 | Nyren |
| 6,274,320 B1 | 8/2001 | Rothberg et al. |
| 6,399,952 B1 | 6/2002 | Maher et al. |
| 6,404,907 B1 | 6/2002 | Gilchrist et al. |
| 6,613,525 B2 | 9/2003 | Nelson et al. |
| 6,780,591 B2 | 8/2004 | Williams et al. |
| 6,828,100 B1 | 12/2004 | Ronaghi |
| 6,833,246 B2 | 12/2004 | Balasubramanian |
| 6,911,327 B2 | 6/2005 | McMillan et al. |
| 6,960,437 B2 | 11/2005 | Enzelberger et al. |
| 7,037,687 B2 | 5/2006 | Williams et al. |
| 7,049,645 B2 | 5/2006 | Sawada et al. |
| 7,133,782 B2 | 11/2006 | Odedra |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,335,762 B2 | 2/2008 | Rothberg et al. |
| 7,348,181 B2 | 3/2008 | Walt et al. |
| 7,424,371 B2 | 9/2008 | Kamentsky |
| 7,535,232 B2 | 5/2009 | Barbaro et al. |
| 7,575,865 B2 | 8/2009 | Leamon et al. |
| 7,645,596 B2 | 1/2010 | Williams et al. |
| 7,782,237 B2 | 8/2010 | Ronaghi et al. |
| 7,785,862 B2 | 8/2010 | Kim et al. |
| 7,835,871 B2 | 11/2010 | Kain et al. |
| 7,875,440 B2 | 1/2011 | Williams et al. |
| 7,948,015 B2 | 5/2011 | Rothberg et al. |
| 8,594,951 B2 | 11/2013 | Homer |
| 9,388,462 B1 | 7/2016 | Eltoukhy |
| 2003/0219797 A1 | 11/2003 | Zhao et al. |
| 2004/0018506 A1 | 1/2004 | Koehler et al. |
| 2004/0197793 A1 | 10/2004 | Hassibi et al. |
| 2004/0197845 A1 | 10/2004 | Hassibi et al. |

(Continued)

FOREIGN PATENT DOCUMENTS

| | | |
|---|---|---|
| GB | 2461127 | 12/2009 |
| JP | 04-262799 | 9/1992 |

(Continued)

OTHER PUBLICATIONS

Li, Heng, "Exploring single-sample SNP and INDEL calling with whole-genome de novo assembly", *Bioinformatics*, 28(14):1838-1844, May 7, 2012.
PCT/US2012/051361, International Preliminary Report on Patentability dated Feb. 27, 2014, 10 pages.
U.S. Appl. No. 13/588,408, Sikora et al.
Svantesson et al., "A mathematical model of the Pyrosequencing reaction system," *Biophysical Chemistry*, 100:129-145 (2004).
454 Sequencing System Software Manual Version 2.6 Part B : *GS Run Processor, GS Reporter, GS Run Browser, GS Support Tool*, available at http://genepool.bio.ed.ac.uk/Gene_Pool/454_software/Manuals/454SeqSys_SWManual-v2.6_PartB_May2011.pdf (last visited Aug. 31, 2012) (document dated May 2011).

(Continued)

*Primary Examiner* — Jerry Lin

(57) ABSTRACT

A method for nucleic acid sequencing includes receiving a plurality of signals indicative of a parameter measured for a plurality of defined spaces, at least some of the defined spaces including one or more sample nucleic acids, the signals being responsive to a plurality of nucleotide flows introducing nucleotides to the defined spaces; determining, for at least some of the defined spaces, whether the defined space includes a sample nucleic acid; processing, for at least some of the defined spaces determined to include a sample nucleic acid, the received signals to improve a quality of the received signals; and predicting a plurality of nucleotide sequences corresponding to respective sample nucleic acids for the defined spaces based on the processed signals and the nucleotide flows.

28 Claims, 21 Drawing Sheets

Specification includes a Sequence Listing.

(56) References Cited

U.S. PATENT DOCUMENTS

| | | |
|---|---|---|
| 2005/0084851 A1 | 4/2005 | Ronaghi et al. |
| 2006/0040297 A1 | 2/2006 | Leamon et al. |
| 2006/0147935 A1 | 7/2006 | Linnarsson |
| 2006/0147983 A1 | 7/2006 | O'uchi et al. |
| 2007/0059733 A1 | 3/2007 | Sundararajan et al. |
| 2007/0059741 A1 | 3/2007 | Kamahori et al. |
| 2007/0092872 A1 | 4/2007 | Rothberg et al. |
| 2007/0207471 A1 | 9/2007 | Osaka et al. |
| 2007/0219367 A1 | 9/2007 | Shchepinov et al. |
| 2007/0281300 A1 | 12/2007 | Russell et al. |
| 2008/0166727 A1 | 7/2008 | Esfandyarpour et al. |
| 2008/0182757 A1 | 7/2008 | Heiner et al. |
| 2008/0286762 A1 | 11/2008 | Miyahara et al. |
| 2008/0286767 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1* | 2/2009 | Roth et al. ............... 435/6 |
| 2009/0105959 A1 | 4/2009 | Braverman et al. |
| 2009/0127589 A1 | 5/2009 | Rothberg et al. |
| 2009/0137404 A1 | 5/2009 | Drmanac et al. |
| 2009/0176200 A1 | 7/2009 | Wakita et al. |
| 2010/0035252 A1 | 2/2010 | Rothberg et al. |
| 2010/0075327 A1 | 3/2010 | Maxham et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0159461 A1* | 6/2010 | Toumazou ...... G01N 27/4148 435/6.11 |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0183320 A1* | 7/2011 | Flusberg et al. ............ 435/6.1 |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0256631 A1 | 10/2011 | Tomaney et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2012/0197623 A1 | 8/2012 | Homer |
| 2013/0060482 A1 | 3/2013 | Sikora et al. |
| 2013/0090860 A1 | 4/2013 | Sikora et al. |
| 2014/0220558 A1 | 8/2014 | Homer |

FOREIGN PATENT DOCUMENTS

| | | |
|---|---|---|
| WO | 1999/019717 | 4/1999 |
| WO | 1999/057321 | 11/1999 |
| WO | 2002/020837 | 3/2002 |
| WO | 2002/024322 | 3/2002 |
| WO | 2003/020895 | 3/2003 |
| WO | 2004/001015 | 12/2003 |
| WO | 2005/040425 | 5/2005 |
| WO | 2007/098049 | 8/2007 |
| WO | 2008/076406 | 6/2008 |
| WO | 2008/092150 | 7/2008 |
| WO | 2008/092155 | 7/2008 |
| WO | 2009/117119 A1 | 9/2009 |
| WO | 2009/158006 | 12/2009 |
| WO | 2010/047804 | 4/2010 |
| WO | 2010/077859 | 7/2010 |
| WO | 2010/117804 | 10/2010 |
| WO | 2010/138182 | 12/2010 |
| WO | 2011/120964 | 10/2011 |
| WO | 2011/156707 | 12/2011 |
| WO | 2012/058459 | 5/2012 |
| WO | 2012/092515 | 7/2012 |

OTHER PUBLICATIONS

Kao et al., "BayesCall: A model-based base-calling algorithm for high-throughput short-read sequencing," *Genome Research*, 19:1884-1895 (2009).

Specification & Drawings of U.S. Appl. No. 61/198,222, filed Nov. 4, 2008.

Appendix to the Specification of U.S. Appl. No. 61/198,222, filed Nov. 4, 2008.

U.S. Appl. No. 13/339,846, Rearick et al.

U.S. Appl. No. 13/339,753, Hubbell.

Ahmadian et al., "Pyrosequencing: History, biochemistry and future," *Clinica Chimica Acta*, 363:83-94 (2006).

Anderson et al., "A System for Multiplexed Direct Electrical Detection of DNA Synthesis," *Sensors and Actuators B: Chemical*, 129(1):79-86 (2008).

Balzer et al., "Characteristics of 454 pyrosequencing data—enabling realistic simulation with flowsim," *Bioinformatics*, 26:i420-i425 (2010).

Barbaro et al., "Fully electronic DNA hybridization detection by a standard CMOS biochip," *Sensors and Actuators B: Chemical*, 118:41-46 (2006).

Brockman et al., "Quality scores and SNP detection in sequencing-by-synthesis systems," *Genome Research*, 18:763-770 (2008).

Chapter 2, "Machine-Learning Foundations: The Probabilistic Framework", In: Baldi, P. and Brunak, S., *Bioinformatics: The Machine Learning Approach*, $2^{nd}$ Edition, The MIT Press, 47-65 (2001).

Eltoukhy et al., "Modeling and Base-Calling for DNA Sequencing-By-Synthesis," *2006 IEEE International Conference on Acoustics, Speech, and Signal Processing*, vol. 2, May 2006, II-1032-II-1035.

Finotello et al., "Comparative analysis of algorithms for whole-genome assembly of pyrosequencing data," *Briefings in Bioinformatics Advance Access*, 1-12 (Oct. 21, 2011).

Hammond et al., "Design of a single-chip pH sensor using a conventional 0.6-μm CMOS process," *IEEE Sensors Journal*, 4:706-712 (2004).

Heer et al., "Single-chip microelectronic system to interface with living cells," *Biosensors and Bioelectronics*, 22:2546-2553 (2007).

Hert et al., "Advantages and limitations of next-generation sequencing technologies: a comparison of electrophoresis and non-electrophoresis methods," *Electrophoresis*, 29(23):4618-26 (2008).

Hizawa et al., "Fabrication of a two-dimensional pH image sensor using a charge transfer technique," *Sensors and Actuators B: Chemical*, 117:509-515 (2006).

Hughes et al., "Chemical Microsensors," *Science*, 254:74-80 (1991).

Huse et al., "Accuracy and quality of massively parallel DNA pyrosequencing," *Genome Biology*, 8(7):R143.1-R143.9 (2007).

Ji et al., "BM-BC: A Bayesian method of base calling for Solexa sequence data," *Department of Biostatistics, The University of Texas M. D. Anderson Cancer Center*, Houston, Texas, U.S.A. (http://odin.mdacc.tmc.edu/~ylji/BMBC/bmbc-ie2.pdf), 1-27, 2010.

Langaee et al., "Genetic variation analyses by Pyrosequencing," *Mutation Research*, 573: 96-102 (2005).

Leamon et al., "Cramming More Sequencing Reactions onto Microreactor Chips," *Chemical Reviews*, 107:3367-3376 (2007).

(56) References Cited

OTHER PUBLICATIONS

Ledergerber et al., "Base-calling for next-generation sequencing platforms," *Briefings in Bioinformatics Advance Access*, 12(5):489-497 (Jan. 18, 2011).

Lysholm et al., "FAAST: Flow-space Assisted Alignment Search Tool," *BMC Bioinformatics* 2011, 12:293 (http://www.biomedcentral.com/1471-2105/12/293), pp. 1-7 (2011).

Margulies et al., Supplementary Methods for the article "Genome sequencing in microfabricated high-density picolitre reactors," *Nature*, 437:376-380 (2005), pp. 1-34.

Margulies et al., "Genome sequencing in microfabricated high-density picolitre reactors," *Nature*, 437:376-380 (2005).

Martinoia et al., "Development of ISFET array-based microsystems for bioelectrochemical measurements of cell populations," *Biosensors and Bioelectronics*, 16:1043-1050 (2001).

Massingham et al., "All Your Base: a fast and accurate probabilistic approach to base calling," *European Bioinformatics Institute, Wellcome Trust Genome Campus*, Hinxton, Cambridgeshire, UK (http://www.ebi.ac.uk/goldman-srv/AYB/references/ayb_revised.pdf), Oct. 26, 2011, 1-26.

Metzker, "Emerging technologies in DNA sequencing," *Genome Research*, 15:1767-1776 (2005).

Milgrew et al., "The development of scalable sensor arrays using standard CMOS technology," *Sensors and Actuators B: Chemical*, 103:37-42 (2004).

Milgrew et al., "A large transistor-based sensor array chip for direct extracellular imaging," *Sensors and Actuators B: Chemical*, 111-112:347-353 (2005).

Mir et al., "Integrated electrochemical DNA biosensors for lab-on-a-chip devices," *Electrophoresis*, 30:3386-3397 (2009).

Pourmand et al., "Direct electrical detection of DNA synthesis," *Proc. Natl. Adac. Sci. U.S.A.*, 103(17):6466-6470 (2006).

Ronaghi, "Pyrosequencing Sheds Light on DNA Sequencing," *Genome Research*, 11:3-11 (2001).

Ronaghi et al., "A Sequencing Method Based on Real-Time Pyrophosphate," *Science*, 281(5375):363-365 (1998).

Trojanowicz, "Recent developments in electrochemical flow detections—a review: part I. Flow analysis and capillary electrophoresis," *Anal. Chim. Acta*, 653(1):36-58 (2009).

Xu et al., "Integration of electrochemistry in micro-total analysis systems for biochemical assays: recent developments," *Talanta*, 80(1):8-18 (2009).

Yeow et al., "A very large integrated pH-ISFET sensor array chip compatible with standard CMOS processes," *Sensors and Actuators B: Chemical*, 44:434-440 (1997).

PCT/US2011/067959, International Search Report and Written Opinion dated Nov. 16, 2012.

PCT/US2012/051361, International Search Report and Written Opinion dated Oct. 23, 2012.

EP12823719.5, Partial European Search Report dated May 12, 2015, 3 pages.

U.S. Appl. No. 13/588,408, Non-Final Office Action dated May 7, 2015, 14 pages.

U.S. Appl. No. 13/645,058, Non-Final Office Action dated Jun. 4, 2015, 7 pages.

EP12823719.5, Extended European Search Report dated Sep. 25, 2015, 12 pp.

\* cited by examiner

METHODS, SYSTEMS, AND COMPUTER READABLE MEDIA FOR NUCLEIC ACID SEQUENCING

CROSS-REFERENCE TO RELATED APPLICATIONS

This application claims priority to U.S. provisional application No. 61/428,733, filed Dec. 30, 2010, which is incorporated by reference herein in its entirety.

The instant application contains a Sequence Listing which has been filed electronically in ASCII format and is hereby incorporated by reference in its entirety. Said ASCII copy, created on DEC. 19, 2018, is named LT00415_SL.txt and is 587 bytes in size.

FIELD

This application generally relates to methods, systems, and computer readable media for nucleic acid sequencing and, more specifically, to methods, systems, and computer readable media for processing and/or analyzing nucleic acid sequencing data and/or signals.

BACKGROUND

Various instruments, apparatuses, and/or systems for sequencing nucleic acids generate large volumes of data that may need to be processed and/or analyzed. Such instruments, apparatuses, and/or systems may include, for example, the Genome Analyzer/HiSeq/MiSeq platforms (Illumina, Inc.; see, e.g., U.S. Pat. Nos. 6,833,246 and 5,750,341); the GS FLX, GS FLX Titanium, and GS Junior platforms (Roche/454 Life Sciences; see, e.g., Ronaghi et al., SCIENCE, 281:363-365 (1998), and Margulies et al., NATURE, 437:376-380 (2005)); and the Ion Personal Genome Machine (PGM™) (Life Technologies Corp./Ion Torrent; see, e.g., U.S. Pat. No. 7,948,015 and U.S. Pat. Appl. Publ. Nos. 2010/0137143, 2009/0026082, and 2010/0282617, which are all incorporated by reference herein in their entirety). In order to increase an overall throughput of nucleic acid sequencing, among other objectives, there is a need for new methods, systems, and computer readable media that allow increases in accuracy, speed, and/or efficiency of processing and/or analyzing of large volumes of nucleic acid sequencing data and/or signals.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIG. 9 discloses SEQ ID NO: 1.

EXEMPLARY EMBODIMENTS

Figure 1:
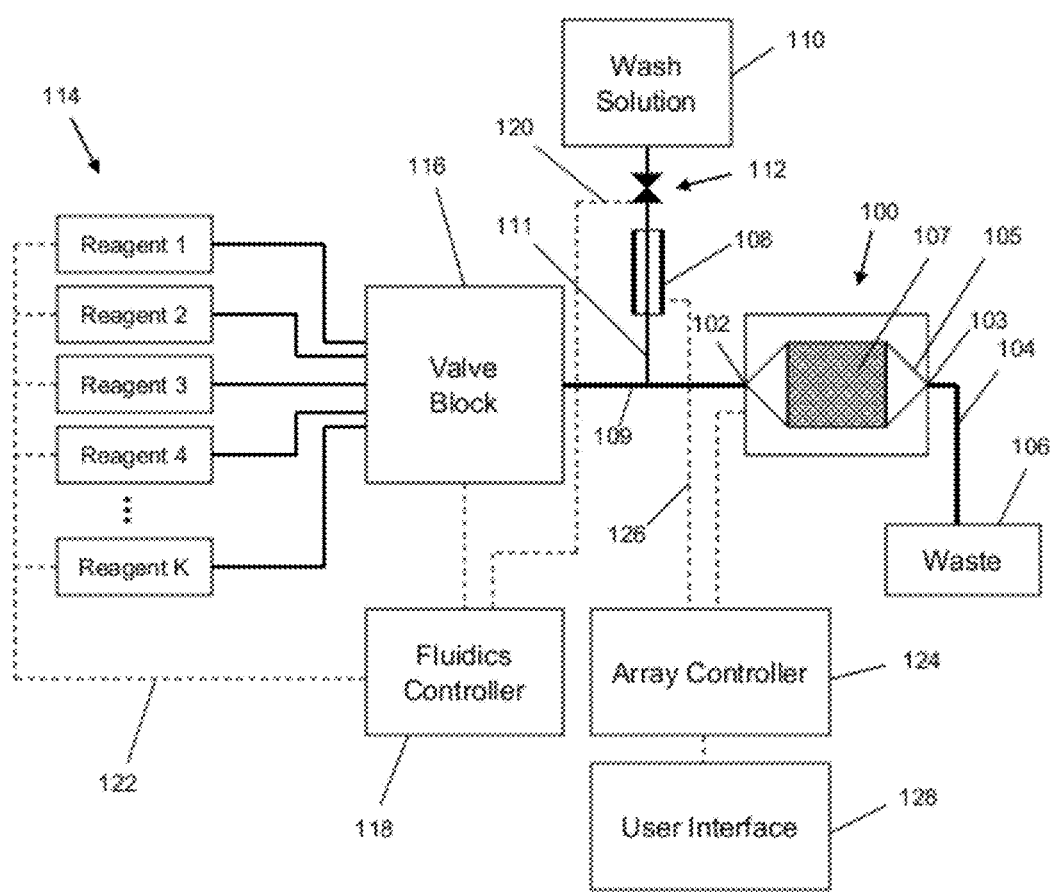
FIG. 1 illustrates components of a system for nucleic acid sequencing according to an exemplary embodiment.

The following description of various exemplary embodiments is exemplary and explanatory only and is not to be construed as limiting or restrictive in any way. Other embodiments, features, objects, and advantages of the present teachings will be apparent from the description and accompanying drawings, and from the claims.

In accordance with the teachings and principles embodied in this application, new methods, systems, and computer readable media for processing and/or analyzing data and/or signals that allow high-throughput sequencing of nucleic acid sequences with increased accuracy, speed, and/or efficiency are provided.

In this application, "amplifying" generally refers to performing an amplification reaction.

In this application, "amplicon" generally refers to a product of a polynucleotide amplification reaction, which includes a clonal population of polynucleotides, which may be single stranded or double stranded and which may be replicated from one or more starting sequences. The one or more starting sequences may be one or more copies of the same sequence, or they may be a mixture of different sequences that contain a common region that is amplified such as, for example, a specific exon sequence present in a mixture of DNA fragments extracted from a sample. Preferably, amplicons may be formed by the amplification of a single starting sequence. Amplicons may be produced by a variety of amplification reactions whose products comprise replicates of one or more starting, or target, nucleic acids. Amplification reactions producing amplicons may be "template-driven" in that base pairing of reactants, either nucleotides or oligonucleotides, have complements in a template polynucleotide that are required for the creation of reaction products. Template-driven reactions may be primer extensions with a nucleic acid polymerase or oligonucleotide ligations with a nucleic acid ligase. Such reactions include, for example, polymerase chain reactions (PCRs), linear polymerase reactions, nucleic acid sequence-based amplifications (NASBAs), rolling circle amplifications, for example, including such reactions disclosed in the following references, which are all incorporated by reference herein in their entirety: Gelfand et al., U.S. Pat. No. 5,210,015; Kacian et al., U.S. Pat. No. 5,399,491; Mullis, U.S. Pat. No. 4,683,202; Mullis et al., U.S. Pat. Nos. 4,683,195; 4,965,188; and 4,800,159; Lizardi, U.S. Pat. No. 5,854,033; and Wittwer et al., U.S. Pat. No. 6,174,670. In an exemplary embodiment, amplicons may be produced by PCRs. Amplicons may also be generated using rolling circle amplification to form a single body that may exclusively occupy a microwell as disclosed in Drmanac et al., U.S. Pat. Appl. Publ. No. 2009/0137404, which is incorporated by reference herein in its entirety.

In this application, "solid phase amplicon" generally refers to a solid phase support, such as a particle or bead, to which is attached a clonal population of nucleic acid sequences, which may have been produced by a process such as emulsion PCR, for example.

In this application, "analyte" generally refers to a molecule or biological cell that can directly affect an electronic sensor in a region (such as a defined space or reaction confinement region or microwell, for example) or that can indirectly affect such an electronic sensor by a by-product from a reaction involving such molecule or biological cell located in such region. In an exemplary embodiment, an analyte may be a sample or template nucleic acid, which may be subjected to a sequencing reaction, which may, in turn, generate a reaction by-product, such as one or more hydrogen ions, that can affect an electronic sensor. The term "analyte" also comprehends multiple copies of analytes, such as proteins, peptides, nucleic acids, for example, attached to solid supports, such as beads or particles, for example. In an exemplary embodiment, an analyte may be a nucleic acid amplicon or a solid phase amplicon. A sample nucleic acid template may be associated with a surface via covalent bonding or a specific binding or coupling reaction, and may be derived from, for example, a shot-gun fragmented DNA or amplicon library (which are examples of library fragments further discussed herein), or a sample emulsion PCR process creating clonally-amplified sample nucleic acid templates on particles such as IonSphere™ particles. An analyte may include particles having attached thereto clonal populations of DNA fragments, e.g., genomic DNA fragments, cDNA fragments, for example.

In this application, "primer" generally refers to an oligonucleotide, either natural or synthetic, that is capable, upon forming a duplex with a polynucleotide template, of acting as a point of initiation of nucleic acid synthesis and being extended from its 3' end along the template so that an extended duplex may be formed. Extension of a primer may be carried out with a nucleic acid polymerase, such as a DNA or RNA polymerase. The sequence of nucleotides added in the extension process may be determined by the sequence of the template polynucleotide. Primers may have a length in the range of from 14 to 40 nucleotides, or in the range of from 18 to 36 nucleotides, for example, or from N to M nucleotides where N is an integer larger than 18 and M is an integer larger than N and smaller than 36, for example. Other lengths are of course possible.

In this application, "oligonucleotide" generally refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, for example. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, for example. In an exemplary embodiment, oligonucleotide may refer to smaller polynucleotides, for example, having 5-40 monomeric units. Polynucleotides may include the natural deoxyribonucleosides (e.g., deoxyadenosine, deoxycytidine, deoxyguanosine, and deoxythymidine for DNA or their ribose counterparts for RNA) linked by phosphodiester linkages. However, they may also include non-natural nucleotide analogs, e.g., including modified bases, sugars, or internucleosidic linkages. In an exemplary embodiment, a polynucleotide may be represented by a sequence of letters (upper or lower case), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes deoxythymidine, and that "I" denotes deoxyinosine, and "U" denotes deoxyuridine, unless otherwise indicated or obvious from context.

In this application, "defined space" (or "reaction space," which may be used interchangeably with "defined space") generally refers to any space (which may be in one, two, or three dimensions) in which at least some of a molecule, fluid, and/or solid can be confined, retained and/or localized. The space may be a predetermined area (which may be a flat area) or volume, and may be defined, for example, by a depression or a micro-machined well in or associated with a microwell plate, microtiter plate, microplate, or a chip. The area or volume may also be determined based on an amount of fluid or solid, for example, deposited on an area or in a volume otherwise defining a space. For example, isolated hydrophobic areas on a generally hydrophobic surface may provide defined spaces. In an exemplary embodiment, a defined space may be a reaction chamber, such as a well or a microwell, which may be in a chip. In an exemplary embodiment, a defined space may be a substantially flat area on a substrate without wells, for example. A defined space may contain or be exposed to enzymes and reagents used in nucleotide incorporation.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. These latter types of reaction confinement regions are referred to herein as microwells or reaction chambers, and may be fabricated using any suitable microfabrication techniques. Reaction confinement regions may also be substantially flat areas on a substrate without wells, for example.

Defined spaces or reaction confinement regions may be arranged as an array, which may be a substantially planar one-dimensional or two-dimensional arrangement of elements such as sensors or wells. The number of columns (or rows) of a two-dimensional array may or may not be the same. Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns. Preferably, each reaction chamber is no greater than 0.34 pL, and more preferably no greater than 0.096 pL or even 0.012 pL in volume. Microwells may have any polygonal cross sections, including square, rectangular, or octagonal cross sections, for example, and may be arranged as a rectilinear array on a surface. Microwells may have hexagonal cross sections and be arranged as a hexagonal array, which permits a higher density of microwells per unit area than rectilinear arrays. An array of defined spaces or reaction confinement regions may be an array of discrete areas on a substantially flat substrate without wells.

A plurality of defined spaces or reaction confinement regions may be arranged in an array, and each defined space or reaction confinement regions may be in electrical communication with at least one sensor to allow detection or measurement of one or more detectable or measurable parameter or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement regions, for example, may be represented as an electrical signal or a voltage, which may be digitalized (e.g., converted to a digital representation of the electrical signal or the voltage). Any of these measurements and representations may be considered raw data or a raw signal. The structure and/or design of sensors for use with the present teachings may vary widely and may include one or more features of the following references, which are all incorporated by reference herein in their entirety: Barbaro et al., U.S. Pat. No. 7,535,232; Esfandyarpour et al., U.S. Pat. Appl. Publ. No. 2008/0166727; Kamahori et al., U.S. Pat. Appl. Publ. No. 2007/0059741; Miyahara et al., U.S. Pat. Appl. Publ. Nos. 2008/0286767 and 2008/0286762; O'uchi, U.S. Pat. Appl. Publ. No. 2006/0147983; Osaka et al., U.S. Pat. Appl. Publ. No. 2007/0207471; Rothberg et al., U.S. Pat. Appl. Publ. No. 2009/0127589; Rothberg et al., U.K. Pat. Appl. No. GB 2461127; and Sawada et al., U.S. Pat. No. 7,049,645.

In this application, "reaction mixture" generally refers to a solution containing any necessary reactants for performing a reaction, which may include, for example, buffering agents to maintain pH at a selected level during a reaction, salts, enzymes, co-factors, scavengers, etc., for example.

In this application, "microfluidics device" generally refers to an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, etc. Microfluidics devices may further include valves, pumps, and specialized functional coatings on interior walls, e.g., to prevent adsorption of sample components or reactants, facilitate reagent movement by electroosmosis, etc. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device may have cross-sectional dimensions of less than a few hundred square micrometers, for example, and passages may have capillary dimensions, e.g., having maximal cross-sectional dimensions of from about 500 µm to about 0.1 µm, for example.

Microfluidics devices may have volume capacities in the range of from 1 µL to a few nL, e.g., 10-100 nL, for example.

In various exemplary embodiments, there are provided methods, systems, and computer readable media for processing and/or analyzing data and/or signals that allow high-throughput sequencing of nucleic acid sequences with increased accuracy, speed, and/or efficiency. The methods, systems, and computer readable media may include steps and/or structural elements for receiving raw data and/or signals, processing the raw data and/or signals using various protocols and modules, and outputting or storing any results in various formats. In an exemplary embodiment, the results may be further processed or analyzed by other methods, systems, and computer readable media.

In various exemplary embodiments, the methods, systems, and computer readable media described herein may advantageously be used to process and/or analyze data and signals obtained from electronic or charged-based nucleic acid sequencing. In electronic or charged-based sequencing (such as, e.g., pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured signals indicative of ion concentration during each nucleotide flow, the identity of the type, sequence and number of nucleotide(s) associated with a sample nucleic acid present in a reaction chamber can be determined.

FIG. 1 illustrates components of a system for nucleic acid sequencing according to an exemplary embodiment. The components include a flow cell and sensor array 100, a reference electrode 108, a plurality of reagents 114, a valve block 116, a wash solution 110, a valve 112, a fluidics controller 118, lines 120/122/126, passages 104/109/111, a waste container 106, an array controller 124, and a user interface 128. The flow cell and sensor array 100 includes an inlet 102, an outlet 103, a microwell array 107, and a flow chamber 105 defining a flow path of reagents over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100. The fluidics controller 118 may control driving forces for the reagents 114 and the operation of valve 112 and valve block 116 with suitable software. The microwell array 107 may include an array of defined spaces or reaction confinement regions, such as microwells, for example, that is operationally associated with a sensor array so that, for example, each microwell has a sensor suitable for detecting an analyte or reaction property of interest. The microwell array 107 may preferably be integrated with the sensor array as a single device or chip. The flow cell may have a variety of designs for controlling the path and flow rate of reagents over the microwell array 107, and may be a microfluidics device. The array controller 124 may provide bias voltages and timing and control signals to the sensor, and collect and/or process output signals. The user interface 128 may display information from the flow cell and sensor array 100 as well as instrument settings and controls, and allow a user to enter or set instrument settings and controls.

In an exemplary embodiment, such a system may deliver reagents to the flow cell and sensor array 100 in a predetermined sequence, for predetermined durations, at predetermined flow rates, and may measure physical and/or chemical parameters providing information about the status of one or more reactions taking place in defined spaces or reaction confinement regions, such as, for example, microwells (or in the case of empty microwells, information about the physical and/or chemical environment therein). In an exemplary embodiment, the system may also control a temperature of the flow cell and sensor array 100 so that reactions take place and measurements are made at a known, and preferably, a predetermined temperature.

In an exemplary embodiment, such a system may be configured to let a single fluid or reagent contact the reference electrode 108 throughout an entire multi-step reaction. The valve 112 may be shut to prevent any wash solution 110 from flowing into passage 109 as the reagents are flowing. Although the flow of wash solution may be stopped, there may still be uninterrupted fluid and electrical communication between the reference electrode 108, passage 109, and the sensor array 107. The distance between the reference electrode 108 and the junction between passages 109 and 111 may be selected so that little or no amount of the reagents flowing in passage 109 and possibly diffusing into passage 111 reach the reference electrode 108. In an exemplary embodiment, the wash solution 110 may be selected as being in continuous contact with the reference electrode 108, which may be especially useful for multi-step reactions using frequent wash steps.

Figure 2A:
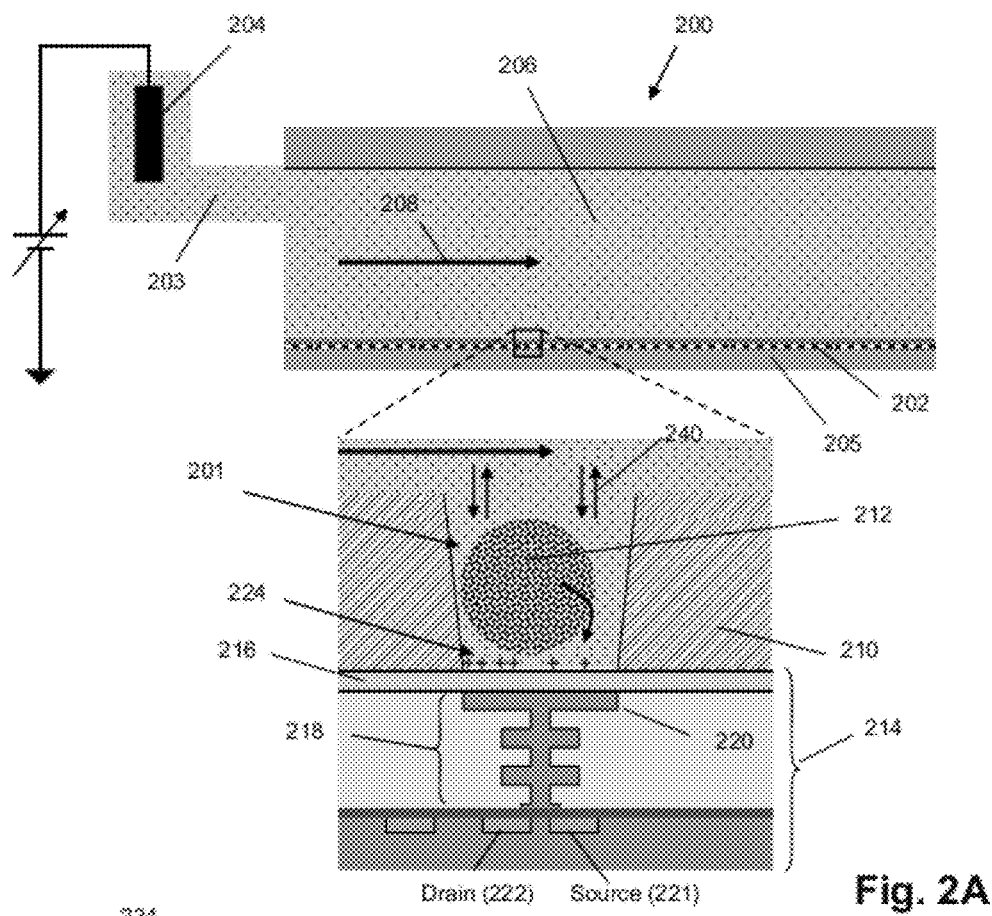
FIG. 2A illustrates cross-sectional and expanded views of a flow cell for nucleic acid sequencing according to an exemplary embodiment.

FIG. 2A illustrates cross-sectional and expanded views of a flow cell 200 for nucleic acid sequencing according to an exemplary embodiment. The flow cell 200 includes a microwell array 202, a sensor array 205, and a flow chamber 206 in which a reagent flow 208 may move across a surface of the microwell array 202, over open ends of microwells in the microwell array 202. A microwell 201 in the microwell array 202 may have any suitable volume, shape, and aspect ratio, which may be selected depending on one or more of any reagents, by-products, and labeling techniques used, and the microwell 201 may be formed in layer 210, for example, using any suitable microfabrication technique. A sensor 214 in the sensor array 205 may be an ion sensitive (ISFET) or a chemical sensitive (chemFET) sensor with a floating gate 218 having a sensor plate 220 separated from the microwell interior by a passivation layer 216, and may be predominantly responsive to (and generate an output signal related to) an amount of charge 224 present on the passivation layer 216 opposite of the sensor plate 220. Changes in the amount of charge 224 cause changes in the current between a source 221 and a drain 222 of the sensor 214, which may be used directly to provide a current-based output signal or indirectly with additional circuitry to provide a voltage output signal. Reactants, wash solutions, and other reagents may move into microwells primarily by diffusion 240. One or more analytical reactions to identify or determine characteristics or properties of an analyte of interest may be carried out in one or more microwells of the microwell array 202. Such reactions may generate directly or indirectly by-products that affect the amount of charge 224 adjacent to the sensor plate 220.

In an exemplary embodiment, a reference electrode 204 may be fluidly connected to the flow chamber 206 via a flow passage 203. In an exemplary embodiment, the microwell array 202 and the sensor array 205 may together form an integrated unit forming a bottom wall or floor of the flow cell 200. In an exemplary embodiment, one or more copies of an analyte may be attached to a solid phase support 212, which may include microparticles, nanoparticles, beads, gels, and may be solid and porous, for example. The analyte may include a nucleic acid analyte, including a single copy and multiple copies, and may be made, for example, by rolling circle amplification (RCA), exponential RCA, or other suitable techniques to produce an amplicon without the need of a solid support.

Figure 2B:
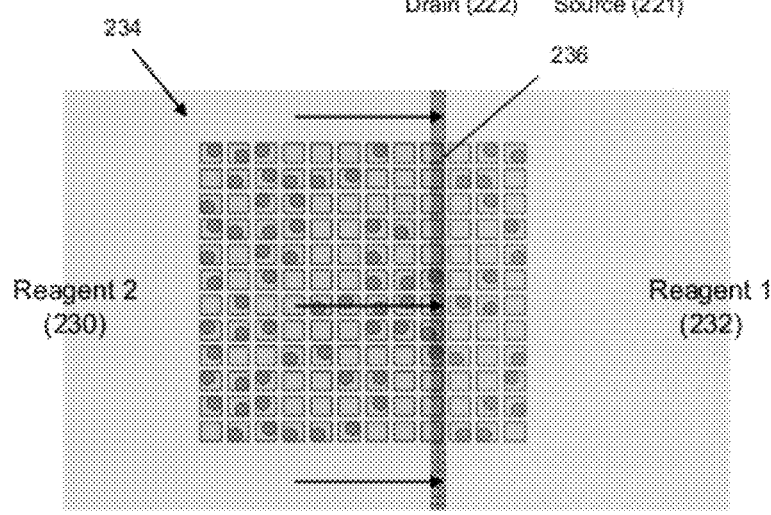
FIG. 2B illustrates a uniform flow front between successive reagents moving across a section of a microwell array according to an exemplary embodiment.

FIG. 2B illustrates a uniform flow front between successive reagents moving across a section 234 of a microwell array according to an exemplary embodiment. A "uniform flow front" between first reagent 232 and second reagent 230 generally refers to the reagents undergoing little or no mixing as they move, thereby keeping a boundary 236 between them narrow. The boundary may be linear for flow cells having inlets and outlets at opposite ends of their flow chambers, or it may be curvilinear for flow cells having central inlets (or outlets) and peripheral outlets (or inlets). In an exemplary embodiment, the flow cell design and reagent flow rate may be selected so that each new reagent flow with a uniform flow front as it transits the flow chamber during a switch from one reagent to another.

Figure 2C:
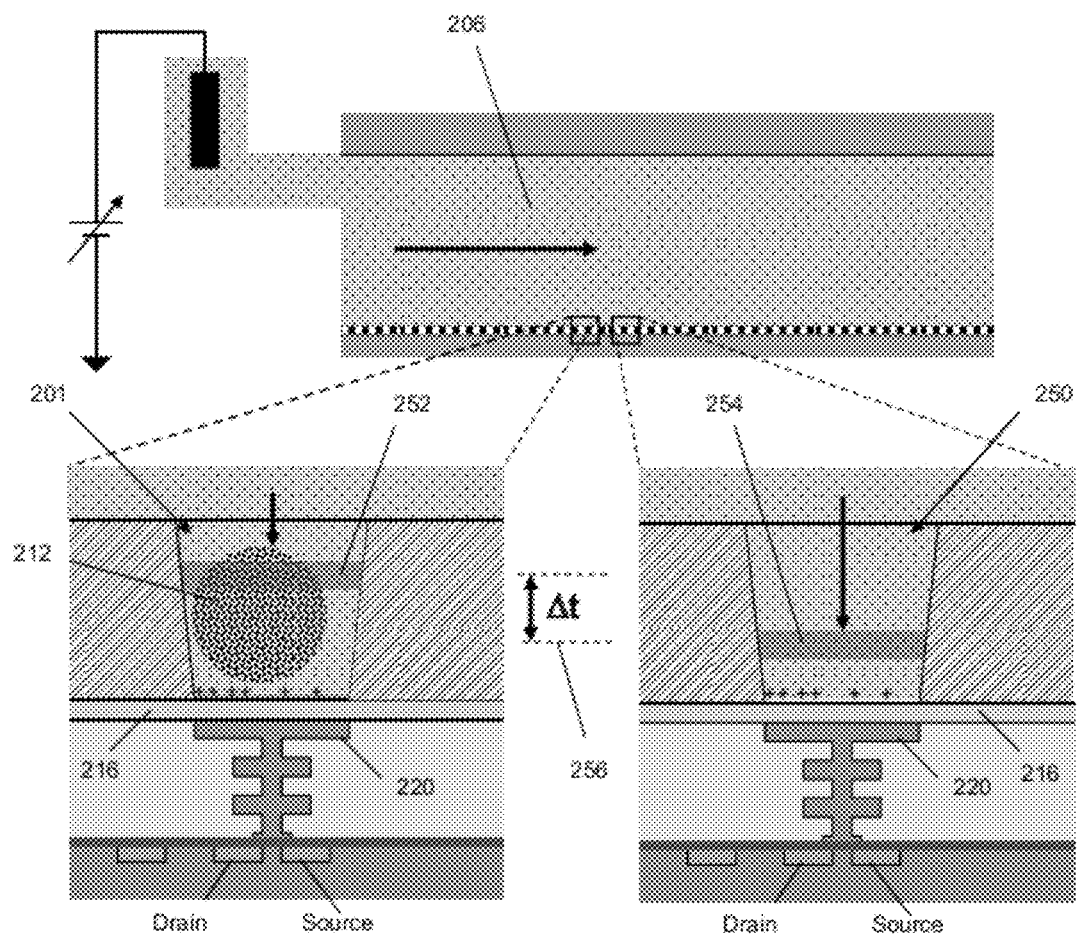
FIG. 2C illustrates a time delay associated with a diffusion of a reagent flow from a flow chamber to a microwell that contains an analyte and/or particle and to an empty microwell according to an exemplary embodiment.

FIG. 2C illustrates a time delay associated with a diffusion of a reagent flow from a flow chamber 206 to a microwell 201 that contains an analyte and/or particle 212 and to an empty microwell 250 according to an exemplary embodiment. The charging reagent flow may diffuse to the passivation layer 216 region opposite of the sensor plate 220. However, a diffusion front 252 of the reagent flow in the microwell 201 containing an analyte and/or particle 212 is delayed relative to a diffusion front 254 of the reagent flow in the empty well 250, either because of a physical obstruction due to the analyte/particle or because of a buffering capacity of the analyte/particle.

In an exemplary embodiment, a correlation between an observed time delay in a change of output signal and the presence of an analyte/particle may be used to determine whether a microwell contains an analyte. To observe the time delay, the pH may be changed using a charging reagent from a first predetermined pH to a different pH, effectively exposing the sensors to a step-function change in pH that will produce a rapid change in charge on the sensor plates. The pH change between the first reagent and the charging reagent (which may sometimes be referred to herein as the "second reagent" or the "sensor-active" reagent) may be 2.0 pH units or less, 1.0 pH unit or less, 0.5 pH unit or less, or 0.1 pH unit or less, for example. The changes in pH may be made using conventional reagents, including HCl, NaOH, for example, at concentrations for DNA pH-based sequencing reactions in the range of from 5 to 200 µM, or from 10 to 100 µM, for example.

Figure 2D:
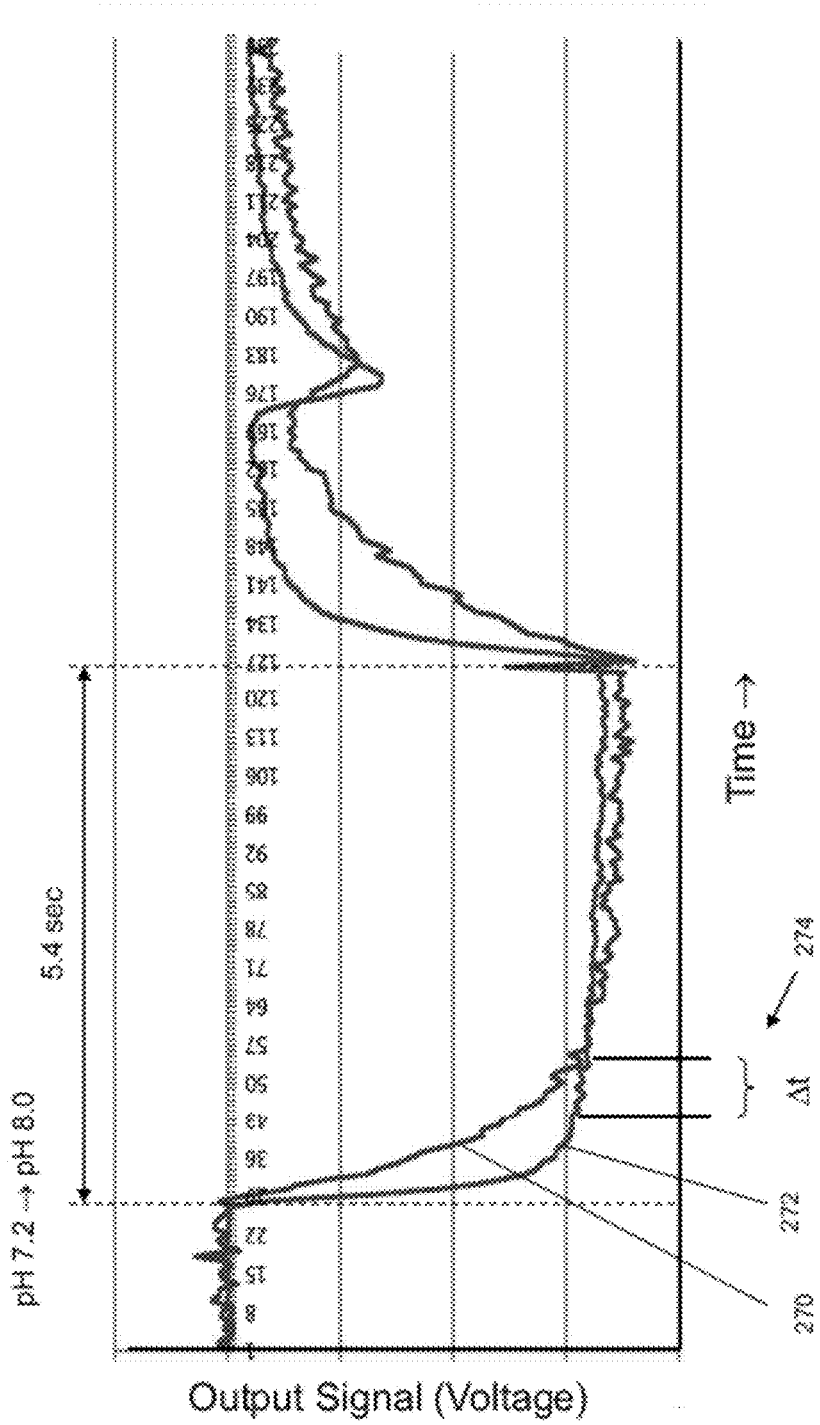
FIG. 2D illustrates a comparison between an output signal from a microwell with a particle and an output signal from a microwell without a particle following a pH change according to an exemplary embodiment.

FIG. 2D illustrates a comparison between an output signal from a microwell with a particle and an output signal from a microwell without a particle following a pH change according to an exemplary embodiment. Curve 270 shows an output signal from a first sensor corresponding to a microwell loaded bead with template, primer, and polymerase attached. Curve 272 shows an output signal from a second sensor corresponding to an empty microwell. The output signals follow a change from pH 7.2 to pH 8.0. Both curves show an abrupt change from a high value corresponding to pH 7.2 to a low value corresponding to pH 8.0. However, the output signal corresponding to the empty microwell reaches the low value noticeably faster than the output signal corresponding to the loaded microwell. The difference in time, Δt 274, at which the respective output signals reach the lower value (or a comparable measure) may be determined with any suitable data analysis techniques, and may be used to determine whether a microwell contains an analyte and/or particle.

Figure 3A:
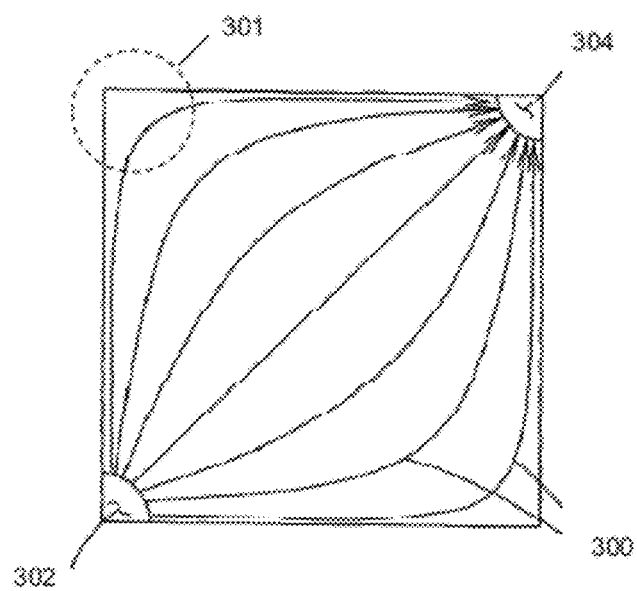
FIG. 3A illustrates flow paths through a flow chamber having diagonally opposed inlet and outlet according to an exemplary embodiment.

FIG. 3A illustrates flow paths through a flow chamber having diagonally opposed inlet and outlet according to an exemplary embodiment. The reagents may follow flow paths 300 as they transit along a diagonal axis of the flow chamber between an inlet 302 and an outlet 304, which paths may not reach all the way to corner 301, for example.

In an exemplary embodiment, a flow cell may direct reagent flows to an array of microwells such that each microwell is exposed to substantially the same flow conditions, such as flow rate and concentration, for example, at substantially the same time throughout the microwell array as reagents are delivered to the array. (As used herein in reference to such exposure, "substantially the same time" generally refers to the transit time through the flow chamber of a boundary between two successive reagents being small in comparison to the length of time a microwell is exposed to any one reagent.)

In an exemplary embodiment, a flow cell may have inlets and outlets located diagonally in a flow chamber constrained to a rectilinear space, and in such a configuration achieving identical flow rates at each microwell may not be possible. Nonetheless, any differences in flow conditions experienced by different microwells, such as flow rate, may then preferably be minimized by a flow chamber and the flow path it defines.

Figure 3B:
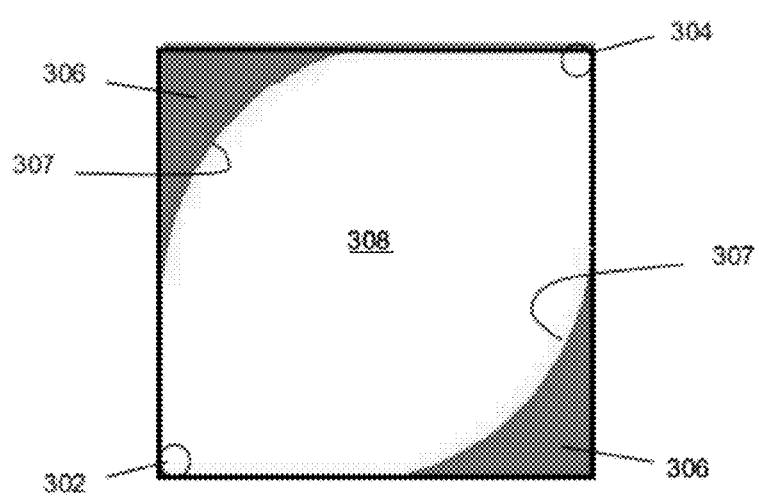
FIG. 3B illustrates a flow chamber with a sensor array area defined by reference to a reach of reagent flow paths according to an exemplary embodiment.

FIG. 3B illustrates a flow chamber 308 with a sensor array area defined by reference to a reach of reagent flow paths according to an exemplary embodiment. The flow chamber may include an area covered by the reagents as they transit from inlet 302 to outlet 304 (excluding an area 306 outside the boundary 307 that delimits an extent of the reagent flow reach in the flow chamber), which area may be used to locate microwells.

Figure 3C:
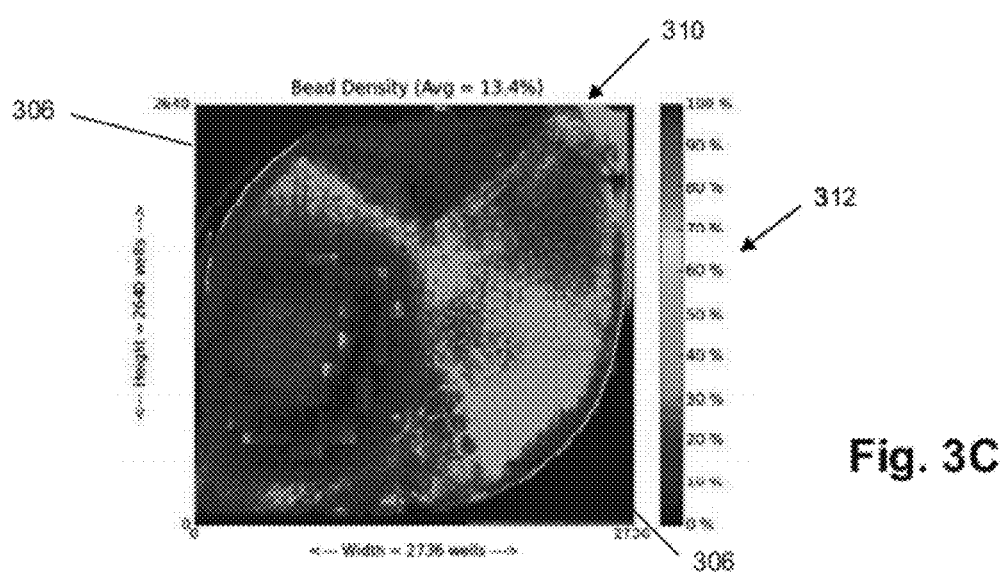
FIG. 3C illustrates a density map of a microwell array in a flow chamber according to an exemplary embodiment.

FIG. 3C illustrates a density map of a microwell array 310 in a flow chamber according to an exemplary embodiment. The density of analyte deposition can be determined by detecting sensor output signal changes responsive to a step-function pH change that can be correlated with a presence or absence of an analyte in a given microwell. The levels of color/darkness in scale 312 indicate a local percentage of microwells (e.g., a percentage of each of many non-overlapping regions of 100 microwells) containing analytes throughout the array, except for unused regions 306.

Figure 4A:
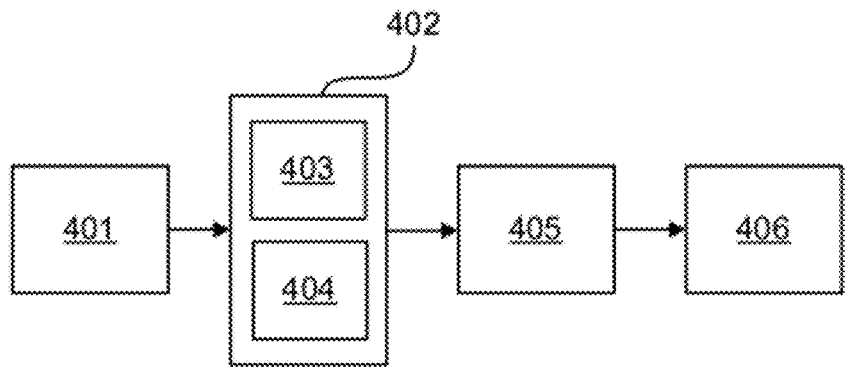
FIG. 4A illustrates a system for processing and/or analyzing nucleic acid sequencing data according to an exemplary embodiment.

FIG. 4A illustrates a system for processing and/or analyzing nucleic acid sequencing data according to an exemplary embodiment. The system includes a sequencing instrument 401, a server 402 or other computing means or resource, and one or more end user computers 405 or other computing means or resource, and may also include other user computers/servers/networks 406. The server 402 may include a processor 403 and a memory and/or database 404. The sequencing instrument 401 and the server 402 may include one or more computer readable media for processing and/or analyzing nucleic acid sequencing data. One or more of these components may be used to perform or implement one or more aspects of the exemplary embodiments described herein.

Figure 4B:
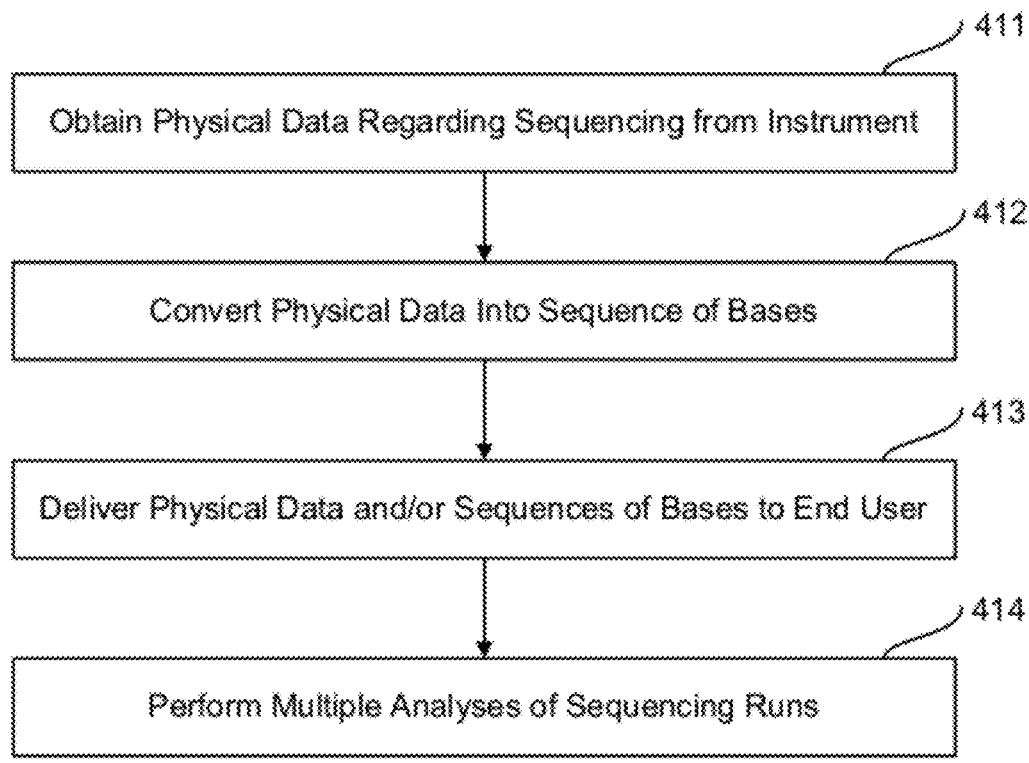
FIG. 4B illustrates a method for processing and/or analyzing nucleic acid sequencing data according to an exemplary embodiment.

FIG. 4B illustrates a method for processing and/or analyzing nucleic acid sequencing data according to an exemplary embodiment. In step 411, a user obtains physical data by performing a sequencing task using a sequencing instrument. The physical data may include voltage data indicative of hydrogen ion concentrations, for example. In step 412, a server or other computing means or resource converts the physical data into sequences of bases. In step 413, the server or other computing means or resource delivers the physical data and/or sequences of bases to an end user. In step 414, if many runs of physical data and/or sequences of bases have been performed, other users and/or entities may perform multiple analyses of sequencing runs. One or more of these steps and/or components may be used to perform or implement one or more aspects of the exemplary embodiments described herein.

Figure 5A:
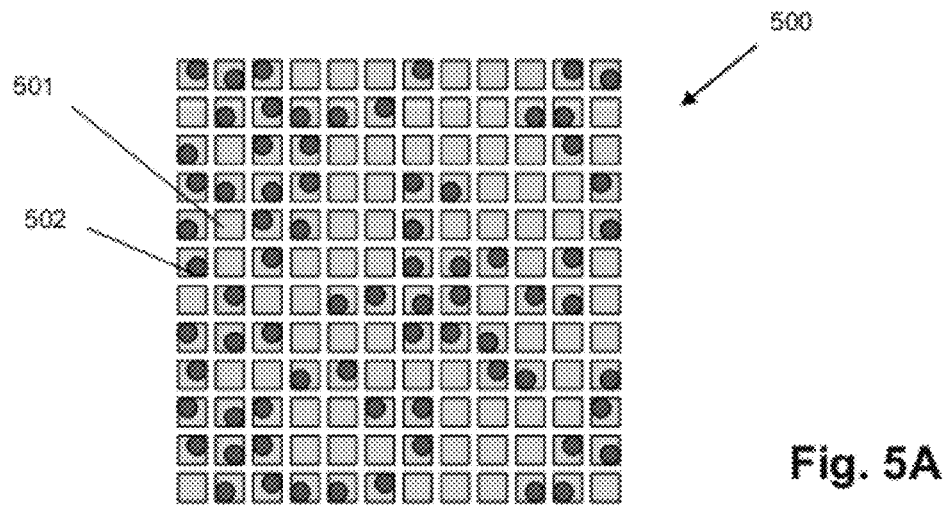
FIG. 5A illustrates an array section including empty microwells and analyte-containing microwells according to an exemplary embodiment.

FIG. 5A illustrates an array section 500 including empty microwells 501 and analyte-containing microwells 502 according to an exemplary embodiment. The analytes may be randomly distributed among the microwells, and may include beads, for example.

In an exemplary embodiment, output signals collected from empty wells may be used to reduce or subtract noise in output signals collected from analyte-containing wells to improve a quality of such output signals. Such reduction or subtraction may be done using any suitable signal processing techniques. The noise component may be measured based on an average of output signals from multiple neighboring empty wells that may be in a vicinity of a well of interest, which may include weighted averages and functions of averages, for example, based on models of physical and chemical processes taking place in the wells.

In an exemplary embodiment, alternatively or in addition to neighboring empty wells, other sets of wells may be analyzed to characterize noise even better, which may include wells containing particles without an analyte, for example. The noise component or averages may be processed in various ways, including converting time domain functions of average empty well noise to frequency domain representations and using Fourier analysis to remove common noise components from output signals from non-empty wells.

Figure 5B:
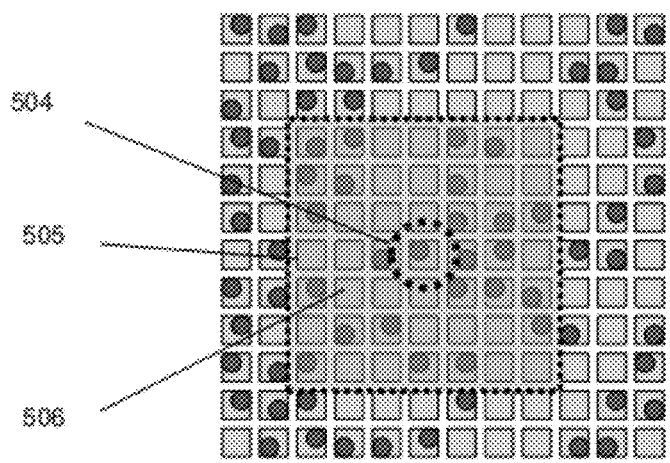
FIGS. 5B and 5C illustrate alternative ways of defining a set of empty microwells in the vicinity of a selected microwell according to an exemplary embodiment.
Figure 5C:
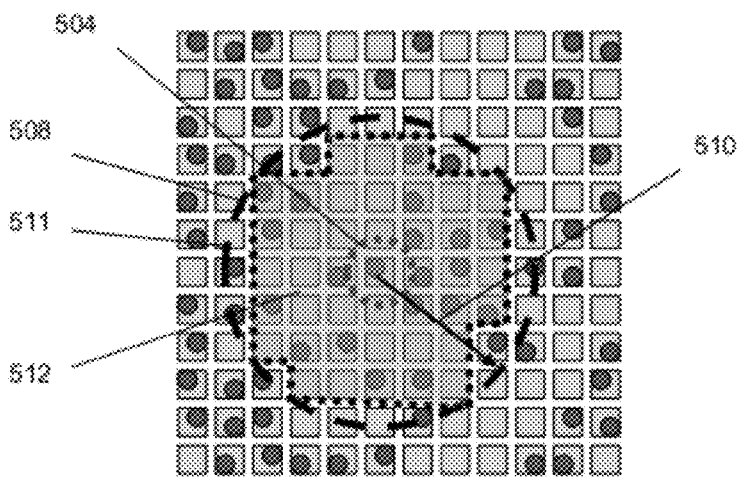

FIGS. 5B and 5C illustrate alternative ways of defining a set of empty microwells in the vicinity of a selected microwell according to an exemplary embodiment. In FIG. 5B, the empty wells to be used are from a fixed region 506 defined by a 7×7 square region of wells 505 for each selected microwell 504. Such a fixed region may vary in the range from 2×2 to 101×101, or in the range from A×A to B×B where A is an integer larger than 2 and B is an integer larger than A and smaller than 101, or in the range from 3×3 to 25×25, for example, or it may be larger in size and may not necessarily be square in shape and could be rectangular, for example. In FIG. 5C, the empty wells to be used may be those wells 508 falling entirely within a circular region 512 defined by a circle 511 having a given radius 510 centered on selected microwell 504. Although all such wells 508 may be used, in some embodiments only a subset of them may actually be used. For example, when analytes or particles are sparsely present (e.g., in less than 25% of the wells), only a portion of the empty wells in a defined region (e.g., 512), which may be a random sample, may be used. The size of such regions may be selected depending on several factors, including a degree of analyte loading, and an availability of computing time/resources, for example.

In an exemplary embodiment, an area and/or number of wells selected for determining an average empty well signal may change according to the density of analytes in the wells. For example, if a minimum of N empty well output signals, e.g., 10, 20, or 30, must be measured to ensure a reliable representation of local noise, then a local region, e.g., 512, may be increased until it contains the necessary number of empty wells. In an exemplary embodiment, local noise may be removed using a fixed area whenever ninety-five percent or less of the wells in an array contain an analyte.

Figure 6A:
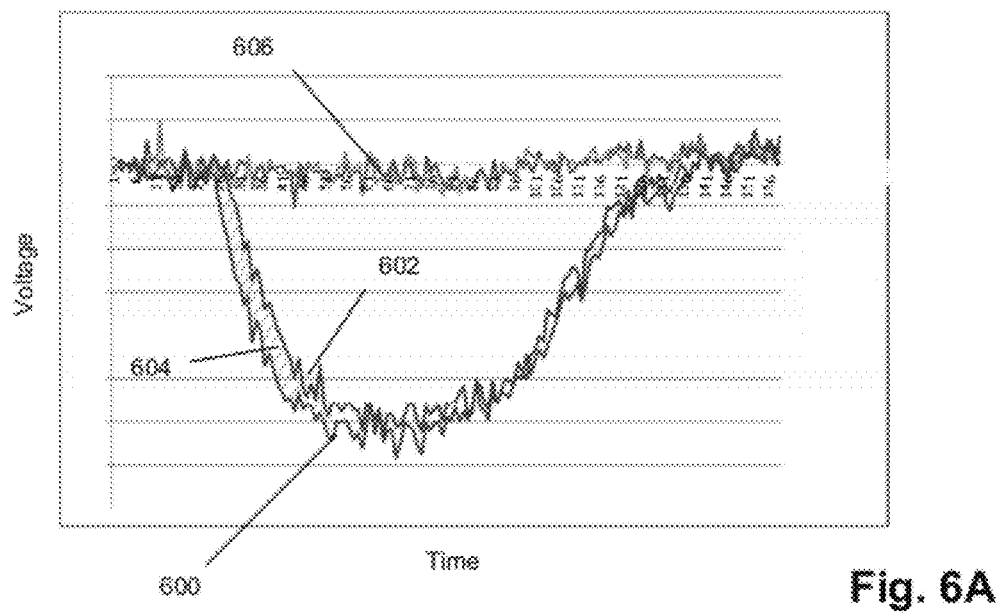
FIG. 6A illustrates various output signals obtained from different wells in response to a reagent change in a pH-based sequencing operation according to an exemplary embodiment.

FIG. 6A illustrates various output signals obtained from different wells in response to a reagent change in a pH-based sequencing operation according to an exemplary embodiment. Curves 606 show signals from wells during a wash step with no changes in reagent. Curve 600 shows an output signal from a well containing a particle with template attached where a primer has been extended by one nucleotide. Curve 602 shows an output signal from a well that contains a particle with a template where there has been no extension. Region 604 shows the difference between signals 602 and 604 that is due to the nucleotide extension. This shows another source of noise (e.g., reagent change noise), which may arise with successive reagent flows. The magnitude of such noise may depend on several factors, including the nature of the measurement being made (e.g., pH, inorganic pyrophosphate (PPi), or other ions), whether a leading or trailing reagent in a reagent change has a property or constituent (e.g., pH) that affects sensor performance and the magnitude of the influence, the relative magnitude of the reagent change effect in comparison with the reaction signal being monitored, etc.

Figure 6B:
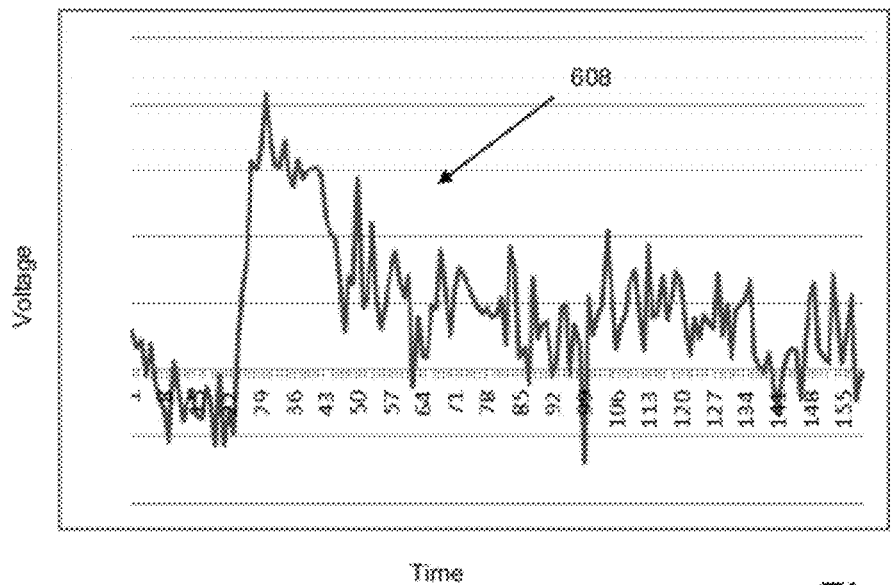
FIG. 6B illustrates a part of an output signal due to a nucleotide incorporation according to an exemplary embodiment.

FIG. 6B illustrates a part of an output signal due to a nucleotide incorporation according to an exemplary embodiment. Curve 608 corresponds to the difference between curves 600 and 602 of FIG. 6A, which corresponds to the part of the raw output signal of curve 600 that is due to the production of an hydrogen ion in the extension reaction. Such reagent change noise (and other noise components common to local groups of wells) may be removed or subtracted from an output signal of a selected well by using output signals of one or more neighboring wells (which may include average values), which may include empty wells and/or non-empty wells where no extension reaction took place. Correction of raw output signals by removal or subtraction of reagent change noise may be carried out after each reagent change based on averages computed after each such change, or using averages from a previous reagent change, depending on the rate at which averages change during a multi-step or multi-cycle electrochemical process, for example. An average may be computed for each different dNTP flow in a sequencing cycle and used to correct raw output signals for from 1 to 5 cycles of reagent change, for example.

Figure 6C:
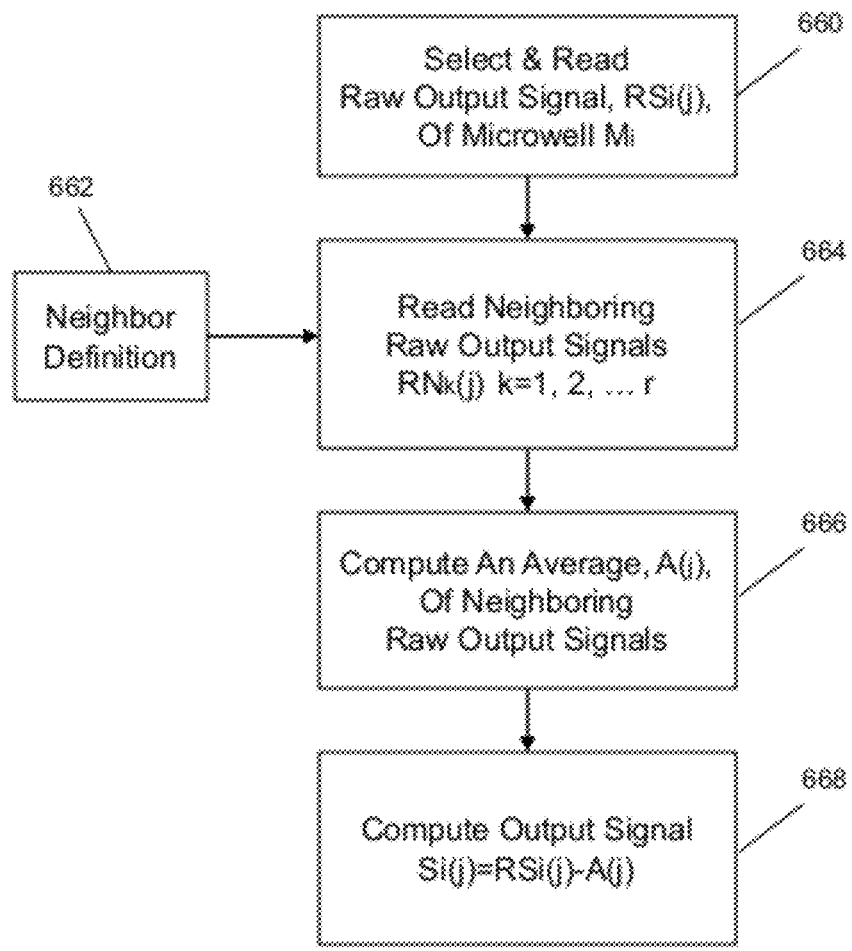
FIG. 6C illustrates a method for removing reagent change noise from a signal according to an exemplary embodiment.

FIG. 6C illustrates a method for removing reagent change noise from a signal according to an exemplary embodiment. In step 660, a raw output signal $RS_i(j)$ for times j=1, 2, ... t and selected well $M_i$ is recorded by a sensor. The raw output signal may represent recorded values of the output signal prior to downstream data processing and/or analysis. In step 662, neighboring wells are defined, which may include definition of a local region as described in FIGS. 5B and 5C, for example, for empty wells or wells with analyte or particle but no reaction, for example. In step 664, raw output signals of neighboring wells $RN_k(j)$ for selected neighbors k=1, 2, ... r are read. The neighboring output signals may be selected from neighboring wells that are physically and chemically similar to the $M_i$ well, except for the presence of a signal from the analyte that is to be detected or measured. In step 666, an average A(j) is computed for the neighboring raw output signals. The average may include weighted averages or transforms of average raw output signals of the neighboring wells to reflect the different physical and chemical conditions of the selected well and its neighbors. In step 668, the average A(j) is subtracted from the raw output signal $RS_i(j)$ to yield a noise-reduced output signal $S_i(j)$.

In an exemplary embodiment, the signal delay shown in FIG. 2D that may permit the detection of empty wells may be accounted for with an appropriate signal transformation in a noise removal process, and an empty well signal may accordingly be modified to account for the absence of a particle and related chemical interactions (including, e.g., an absence of delay and flattening that would occur in an analyte-containing well).

Figure 6D:
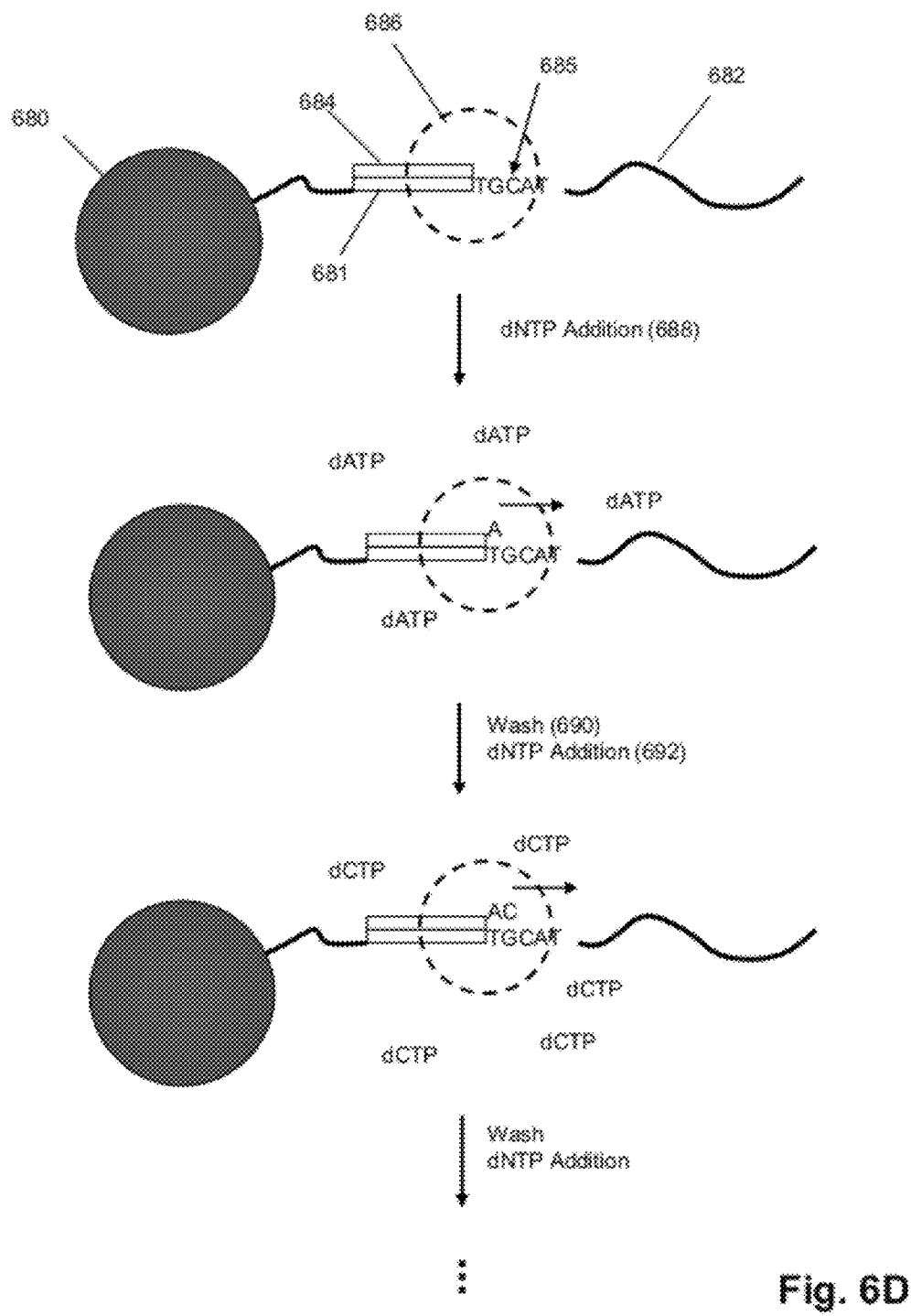
FIG. 6D illustrates schematically a process for label-free, pH-based sequencing according to an exemplary embodiment.

FIG. 6D illustrates schematically a process for label-free, pH-based sequencing according to an exemplary embodiment. A template 682 with a primer binding site 681 are attached to a solid phase support 680. The template 682 may be attached as a clonal population to a solid support, such as a microparticle or bead, for example, and may be prepared as disclosed in U.S. Pat. No. 7,323,305, which is incorporated by reference herein in its entirety. A primer 684 and DNA polymerase 686 are operably bound to the template 682. As used herein, "operably bound" generally refers to a primer being annealed to a template so that the primer's 3' end may be extended by a polymerase and that a polymerase is bound to such primer-template duplex (or in close proximity thereof) so that binding and/or extension may take place when dNTPs are added. In step 688, dNTP (shown as dATP) is added, and the DNA polymerase 686 incorporates a nucleotide "A" (since "T" is the next nucleotide in the template 682). In step 690, a wash is performed. In step 692, the next dNTP (shown as dCTP) is added, and the DNA polymerase 686 incorporates a nucleotide "C" (since "G" is the next nucleotide in the template 682). The pH-based nucleic acid sequencing, in which base incorporations may be determined by measuring hydrogen ions that are generated as natural by-products of polymerase-catalyzed extension reactions, may be performed using at least in part one or more features of Anderson et al., Sensors and Actuators B Chem., 129:79-86 (2008); Rothberg et al., U.S. Pat. Appl. Publ. No. 2009/0026082; and Pourmand et al., Proc. Natl. Acad. Sci., 103:6466-6470 (2006), which are all incorporated by reference herein in their entirety. In an exemplary embodiment, after each addition of a dNTP, an additional step may be performed in which the reaction chambers are treated with a dNTP-destroying agent, such as apyrase, to eliminate any residual dNTPs remaining in the chamber that might result in spurious extensions in subsequent cycles.

The output signals measured throughout this process depend on the number of nucleotide incorporations. Specifically, in each addition step, the polymerase extends the primer by incorporating added dNTP only if the next base in the template is complementary to the added dNTP. If there is one complementary base, there is one incorporation; if two, there are two incorporations; if three, there are three incorporations, and so on. With each incorporation, an hydrogen ion is released, and collectively a population released hydrogen ions change the local pH of the reaction chamber. The production of hydrogen ions is monotonically related to the number of contiguous complementary bases in the template (as well as to the total number of template molecules with primer and polymerase that participate in an extension reaction). Thus, when there is a number of contiguous identical complementary bases in the template (which may represent a homopolymer region), the number of hydrogen ions generated and thus the magnitude of the local pH change is proportional to the number of contiguous identical complementary bases (and the corresponding output signals are then sometimes referred to as "1-mer," "2-mer," "3-mer" output signals, etc.). If the next base in the template is not complementary to the added dNTP, then no incorporation occurs and no hydrogen ion is released (and the output signal is then sometimes referred to as a "0-mer" output signal). In each wash step of the cycle, an unbuffered wash solution at a predetermined pH may be used to remove the dNTP of the previous step in order to prevent misincorporations in later cycles. In an exemplary embodiment, the four different kinds of dNTP are added sequentially to the reaction chambers, so that each reaction is exposed to the four different dNTPs, one at a time. In an exemplary embodiment, the four different kinds of dNTP are added in the following sequence: dATP, dCTP, dGTP, dTTP, dATP, dCTP, dGTP, dTTP, etc., with each exposure followed by a wash step. Each exposure to a nucleotide followed by a washing step can be considered a "nucleotide flow." Four consecutive nucleotide flows can be considered a "cycle." For example, a two cycle nucleotide flow order can be represented by: dATP, dCTP, dGTP, dTTP, dATP, dCTP, dGTP, dTTP, with each exposure being followed by a wash step. Different flow orders are of course possible.

In an exemplary embodiment, template 682 may include a calibration sequence 685 that provides a known signal in response to the introduction of initial dNTPs. The calibration sequence 685 preferably contains at least one of each kind of nucleotide, may contain a homopolymer or may be non-homopolymeric, and may contain from 4 to 6 nucleotides in length, for example. In an exemplary embodiment, calibration sequence information from neighboring wells may be used to determine which neighboring wells contain templates capable of being extended (which may, in turn, allows identification of neighboring wells that may generate 0-mer signals, 1-mer signals, etc., in subsequent reaction cycles), and may be used to remove or subtract undesired noise components from output signals of interest.

In an exemplary embodiment, an average 0-mer signal may be modeled (which may be referred to herein as a "virtual 0-mer" signal) by taking into account (i) neighboring empty well output signals in a given cycle, and (ii) one or more effects of the presence of a particle and/or template on the shape of the reagent change noise curve (such as, e.g., the flattening and shifting in the positive time direction of an output signal of a particle-containing well relative to an output signal of an empty well, as reflected in FIG. 2D). Such effects may be modeled to convert empty well output signals to virtual 0-mer output signals, which may in turn be used to subtract reagent change noise.

Figure 6E:
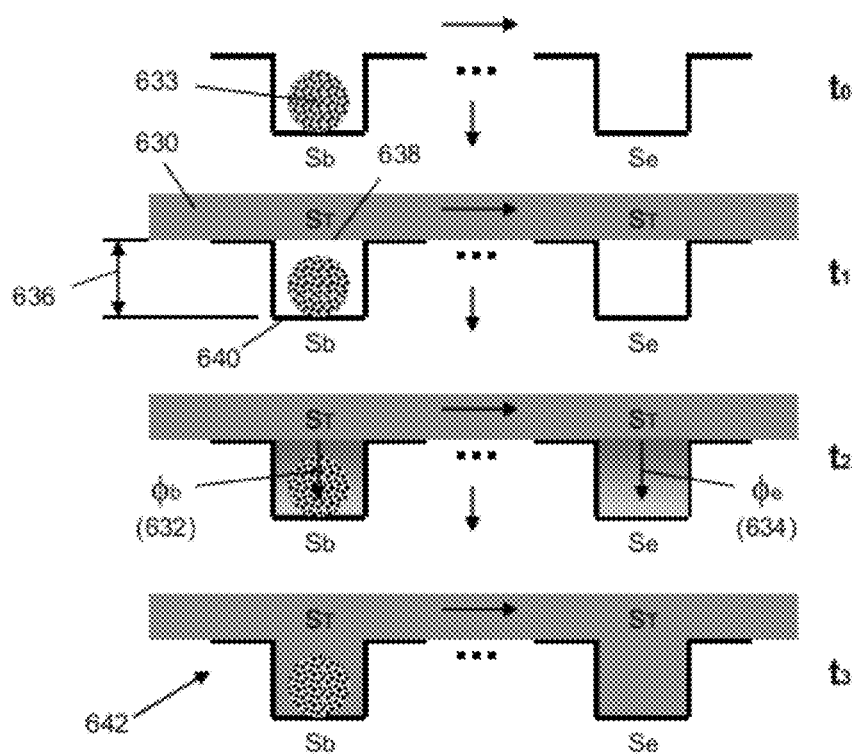
FIG. 6E illustrates a model for using an average neighbor signal to remove reagent change noise from a signal according to an exemplary embodiment.

FIG. 6E illustrates a model for using an average neighbor signal to remove reagent change noise from a signal according to an exemplary embodiment. Shown are neighboring wells at four different times during a reagent change: $t_0$ (before a next reagent is added), $t_1$ (immediately after the next reagent is added), $t_2$ (during equilibration of the next reagent with the well contents), and $t_3$ (after equilibrium has been achieved). The change in sensor signal is described as a two compartment model, where one compartment is the next reagent (e.g., the next flow of dNTPs) in region 638 adjacent to the opening of a well and the other compartment is the surface 640 at the bottom of a well adjacent to the sensor. Immediately after new reagent 630 enters, a concentration difference 636 is created between the two compartments, so that a flux of hydrogen ions is established both in wells with particles $\varphi_b$ 632 and in empty wells $\varphi_e$ 634. For microwells having particles 633 where extension reactions occur, hydrogen ions are also created, which adds to the flux. Eventually equilibrium 642 is reached and the flux of hydrogen ions goes to zero. A variety of alternative models of differing complexity may be used to describe the physical and chemical phenomena of the electrochemical reactions taking place in the wells.

In an exemplary embodiment, the generation of hydrogen ions by extension reactions and the fluxes through wells with and without particles/beads may be described by equations including the following reaction-diffusion equations:

$$\frac{S_T - S_b}{\alpha_b} = \varphi_b = \frac{\delta S_b}{\delta t}\beta_b$$

$$\frac{S_T - S_e}{\alpha_e} = \varphi_e = \frac{\delta S_e}{\delta t}\beta_e$$

In these equations, $S_T$ refers to the signal measured at the top of the wells, which corresponds to the flowing solution; $S_b$ refers to the signal measured from the bottom of the loaded well; $S_e$ refers to the signal measured from the bottom of the empty well; $\alpha_b$ and $\alpha_e$ are diffusion constants of the hydrogen ions in the solution; and $\beta_b$ and $\beta_e$ are constants that reflect the interaction (e.g., buffering) of the hydrogen ions with the well and/or particle or analyte in the well. Manipulation of these terms and integration yields $S_b$ as a function of $S_e$ and an integral of the difference between $S_e$ and $S_b$, plus a source term, $I_{ext}$, for the hydrogen ions generated in an extension reaction, which can be expressed using the following equation:

$$S_b = S_e R + \frac{\int S_e - S_b}{\tau_b} + I_{ext}$$

In this equation, $R = \tau_e/\tau_b$ where $\tau_e = \alpha_e \beta_e$ and $\tau_b = \alpha_b \beta_b$. Curves for $S_b$ can be generated numerically for fitting data to remove reagent change noise.

Figure 6F:
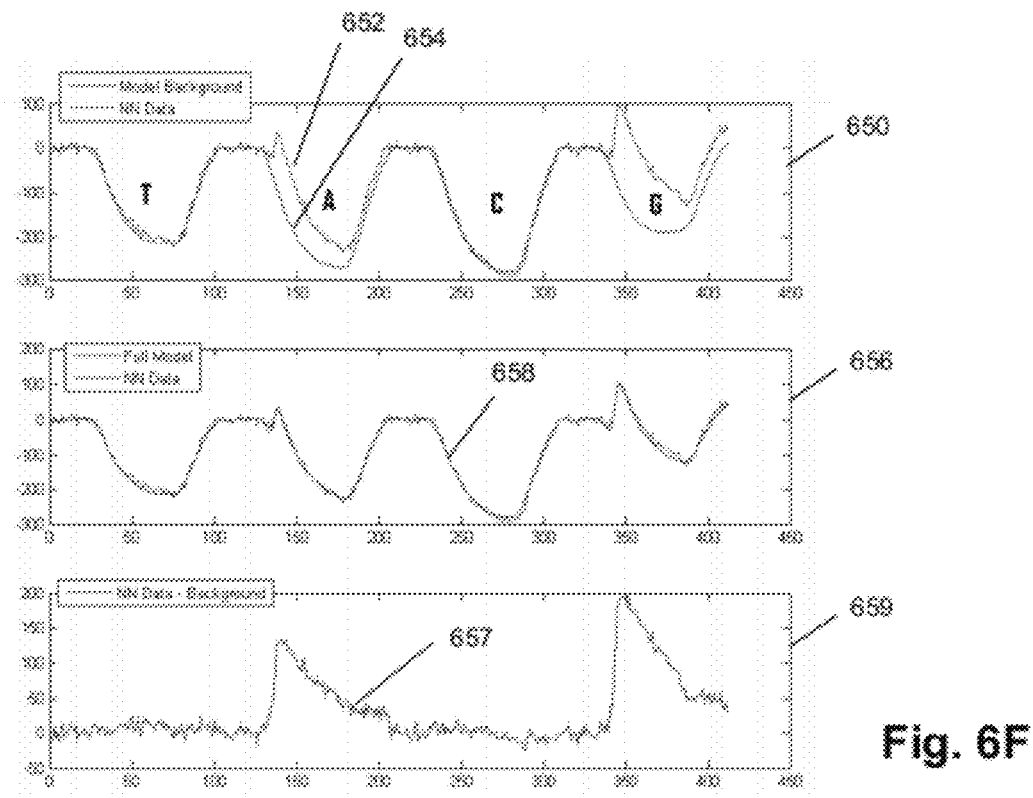
FIG. 6F illustrates data fit by a model such as presented in FIG. 6E and use of such model to subtract reagent change noise from an incorporation signal according to an exemplary embodiment.

FIG. 6F illustrates data fit by a model such as presented in FIG. 6E and use of such model to subtract reagent change noise from an incorporation signal according to an exemplary embodiment. Panel 650 shows an output signal 652 ("NN Data") from a sensor of a well in which extension reactions occur when exposed to flows of dATP and dGTP. Curve 654 ("Model Background") shows a reagent change noise background component (which component may be represented in the model by the first two terms on the right of the expression for $S_b$) from the above model. Panel 656 includes curve 658, which shows both the reagent change noise and the generation of hydrogen ions (which may be represented in the model by the entire expression for $S_b$), and that such complete model nearly overlaps with the "NN Data" curve. Panel 659 shows output signal 657, after removal of the reagent change noise background component, which more clearly shows the signal due to nucleotide incorporations.

Figure 7:
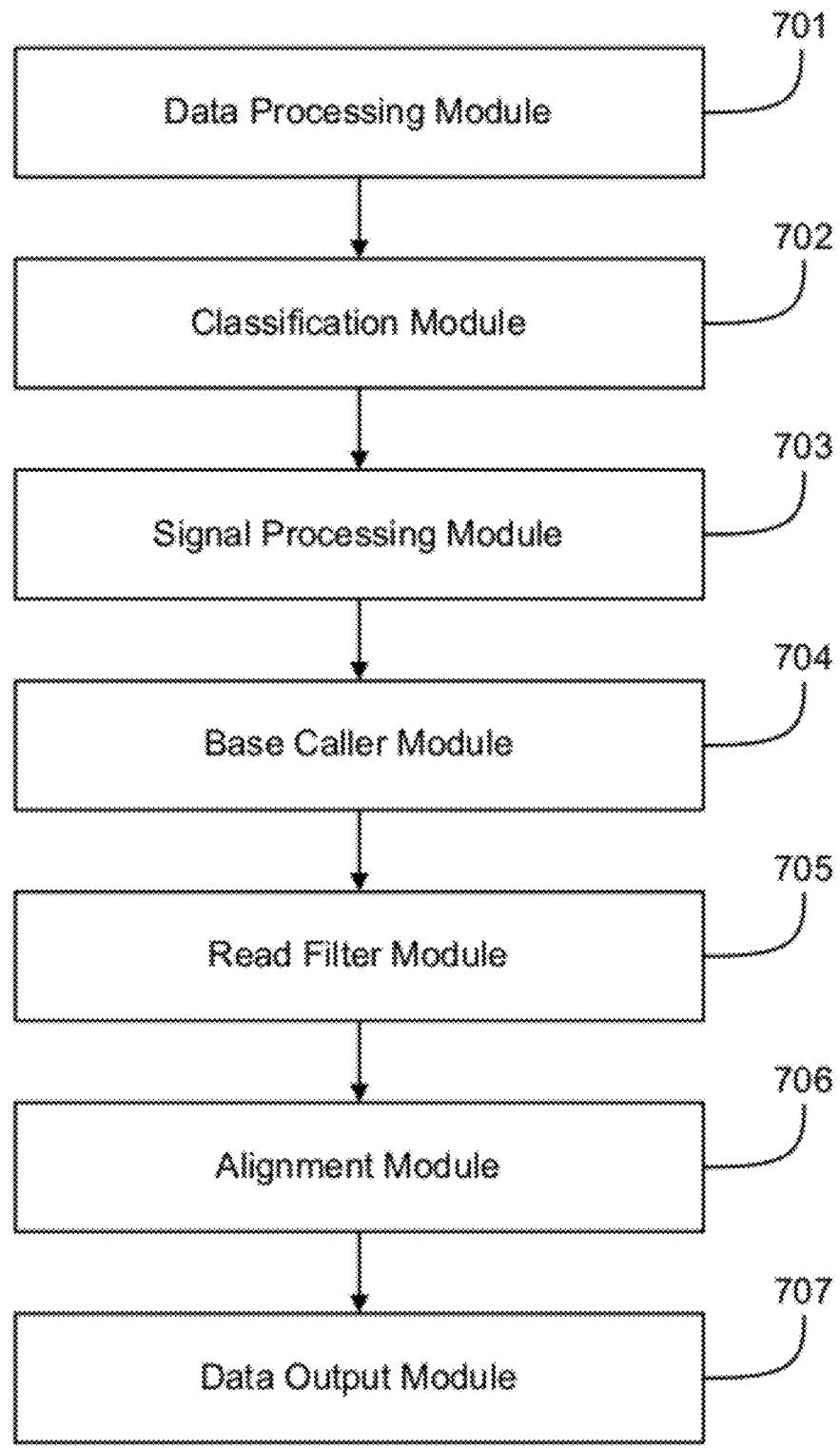
FIG. 7 illustrates a system for nucleic acid sequencing according to an exemplary embodiment.

FIG. 7 illustrates a system for nucleic acid sequencing according to an exemplary embodiment. The system includes a data processing module 701, a classification module 702, a signal processing module 703, a base caller module 704, a read filter module 705, an alignment module 706, and a data output module 707. The system may be implemented in one or more computers and/or servers and may be accessible at least in part through a web-accessible data portal. In an exemplary embodiment, there is provided a method performing steps including the general steps associated with modules 701-707 (e.g., processing data, classifying defined spaces or reaction confinement regions, processing signals, calling bases, filtering reads, aligning reads, and outputting results).

Data Processing Module

In an exemplary embodiment, a data processing module or data processor may be configured to receive data (e.g., raw data, which may be a series of signals), which may be reflective or indicative of one or more by-product(s) of a chemical reaction. The signals may be derived from nucleotide incorporation events (e.g., incorporation of a dNTP associated with a sample nucleic acid template) by measuring hydrogen ions generated as by-products of polymerase-catalyzed nucleic acid extension reactions. The hydrogen ion concentration (or pH) for a defined space or reaction confinement region may be measured repeatedly and at intervals timed to coincide with the nucleotide flows of different types of dNTPs. The signals may be actual raw pH values, or they may be a conversion of the raw pH value (or related physical measurement) in each defined space into a voltage, for example, which may then be converted into a digital representation.

The data processing module may be configured to generate one or more acquisition file(s) for the raw data, which may contain raw signals from defined spaces of a chip, for example, for one or more nucleotide flow(s). For a chip containing about 1.5 million wells, for example, each nucleotide flow can result in about 1.5 million separate nucleotide incorporation events, and a series of such acquisition files can represent about 1.5 million possible reads. A read can represent consecutive base calls associated with a sequence of a nucleic acid. A read can reflect bases or base complements associated with a sample nucleic acid template, which can be associated with a defined volume, such as a well, or with a defined area, such as a portion of a surface of a substantially flat substrate, for example. A read can include a full sequence of the sample nucleic acid template or a portion thereof. A read can include about eight nucleotides (base calls) and can contain 16 or more base calls, 25 or more base calls, 50 or more base calls, 100 or more base calls, or 120 or more base calls, for example. The length of a read can be expressed as a number of base pairs (bps).

In an exemplary embodiment, the data processing module may be configured to perform multiple functions, including receiving or loading raw data and/or signals (which may be temporarily or permanently stored in a memory and may be compressed and decompressed as desired), decompiling raw data, and offset correcting raw data. For example, the raw data and/or signals may be streamed off of an analytical instrument directly to the data processing module. Alternatively, or in combination with direct steaming, the data processing module may access or receive the raw data and/or signals after storage or collection on a computer-readable medium, such as a portable disk or hard drive, for example. The data processing module may receive directly raw acquisition files in DAT file format (e.g., acq_*.dat files), for example, streaming from an analytical instrument.

In an exemplary embodiment, the data processing module may be configured to compress data and/or signals using one or more compression modes, which may include a dynamic/ variable frame rate compression mode and a key frame and/or delta compression mode. In the dynamic/variable frame rate compression mode, certain portions of a nucleotide incorporation event or a nucleotide flow may be captured at different frame rates to allow capture of biologically specific events at high resolution while reducing the overall file size by allowing multiple frames in some portions to be averaged. In the key frame and/or delta compression mode, whereas an initial value is actually stored, for subsequent values only their difference relative to the initial value may be stored.

In an exemplary embodiment, the data processing module may be configured to perform raw signal offset and/or background corrections. Each defined space may have its own reference value. To compare two defined spaces, a common reference may be used. The offset and/or background correction can take the average of the first few frames within each acquisition file, and subtract that value from values for each defined space, thus allowing measurements within the defined space to have a common reference value.

In an exemplary embodiment, the data processing module may flag or exclude certain defined spaces that may for whatever reason not be functional or may be covered, obscured, or otherwise fluidically inaccessible or unaddressable. For example, a mask may be loaded, per chip type, to mark those defined spaces as excluded so as to avoid unnecessary and/or computationally inefficient downstream processing of the chip and signals generated therefrom, where the information likely will be uninformative.

Classification Module

In an exemplary embodiment, a classification module or classifier may be configured to classify one or more wells of an array as to whether the well is empty or contains an analyte or substrate associated with an analyte and whether the well generally contains useful information that should be carried forward and included in downstream processing and/or analysis. Because the data can include signals from thousands to millions of individual wells, reducing the amount of data to be carried forward can increase overall performance and efficiency, and conserve file storage space. (Of course, in practice while some data can be screened, all data may be stored so that various screening and manipulating of the data can be started anew, if desired.) The classification module may process wells in smaller groups or regions rather than as one group to exploit parallel computing techniques, such as multi-core and/or multi-process nodes that have parallel computational capabilities. For example, a chip containing an array of about 1.5 million wells can be segmented into 50×50 well regions, resulting in about 625 total regions.

In an exemplary embodiment, the classification module may be configured to classify one or more wells of an array as to whether the well is empty or contains an analyte or substrate associated with an analyte by flowing a known pH buffer at a different pH than a wash buffer onto the wells. If the diffusion rate in the well is slower than an average rate of surrounding neighbors, for example, then the well may be considered to contain a particle. If not, then the well may be identified as empty. Other procedures to establish a baseline pH change over time can include, for example, fitting the signal to exponentials or other models of the expected background signal.

According to an exemplary embodiment, there is provided a method for determining whether a defined space includes an analyte or substrate associated with an analyte, including: (1) changing reagents in a flow chamber from a first reagent that sensors generate in response thereto a first output signal to a second reagent that sensors generate in response thereto a second output signal; and (2) correlating a time delay in the generation of the second output signal in response to the changing of reagents with a presence or absence of an analyte or substrate associated with an analyte. In such a method, the sensor may be an electrochemical sensor, including a potentiometric sensor, an impedimetric sensor, or an amperometric sensor, for example, or any sensor such that the output signal depends on an interaction between an electrode or other analyte-sensitive surface and a sensor-active reagent whose arrival is delayed by physical or chemical obstructions in a defined space. The sensor-active reagent may be a wash solution at a different pH than the reagent it replaces, which may also be the wash solution.

In an exemplary embodiment, the classification module may be further configured to identify and parse sample nucleic acids or fragments based on their type and/or origin. Such identification, which may be useful when using test nucleic acid fragments as a control and/or when pooling and sequencing fragmented samples of nucleic acids from different origin ("multiplexing"), for example, may be based on labeling or tagging of the fragments prior to the sequencing process (e.g., with fluorescent tags). In an exemplary embodiment, such identification may be performed using sequencing keys (e.g., a known artificial nucleic acid sequence, as discussed below).

Figure 8:
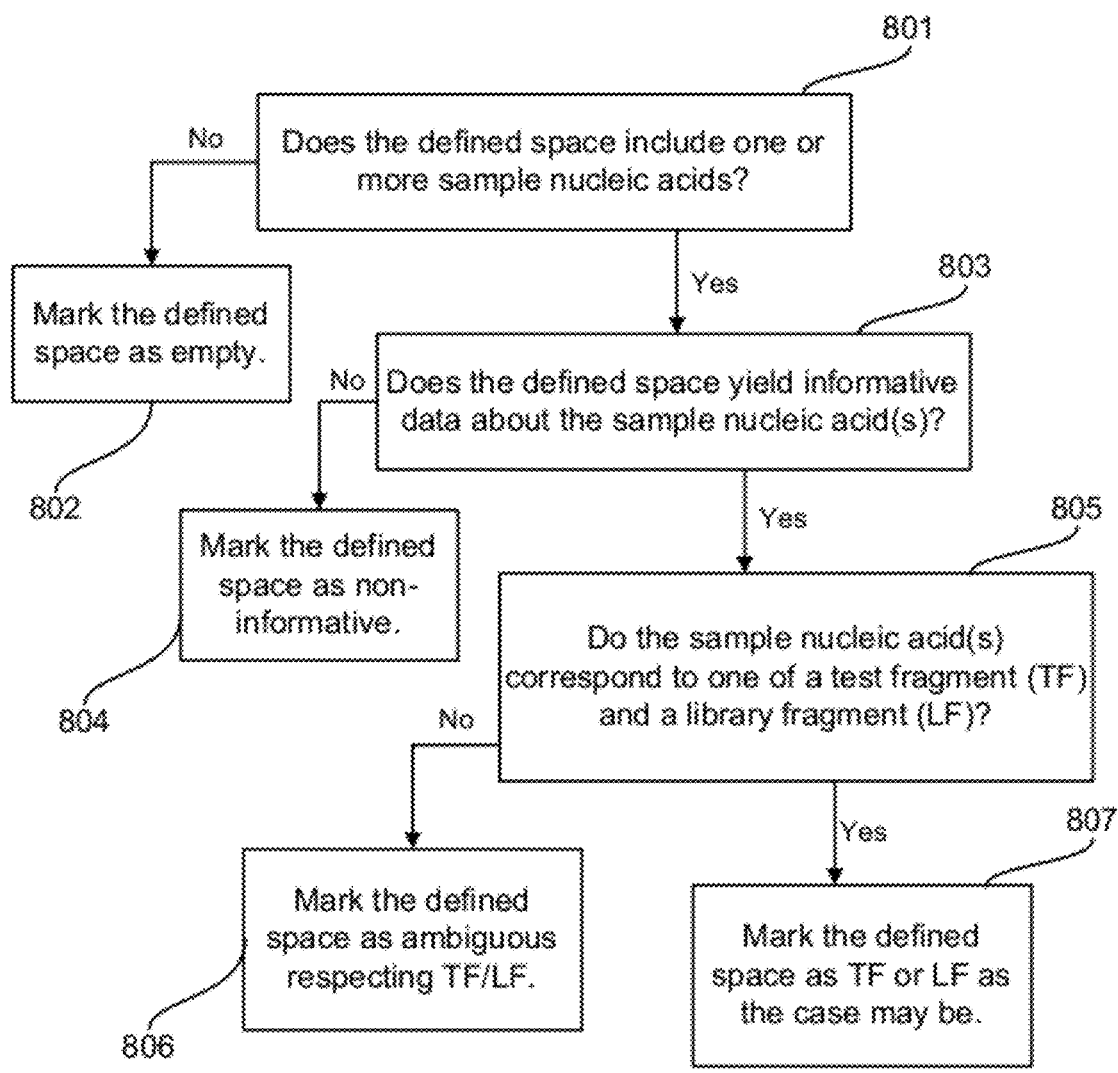
FIG. 8 illustrates a method for classifying a content of a defined space according to an exemplary embodiment.

FIG. 8 illustrates a method for classifying a content of a defined space according to an exemplary embodiment. In step 801, a module or other hardware and/or software component considers whether a defined space includes one or more nucleic acids, which may be associated with a solid substrate such as a bead. In step 802, if the answer is no, the defined space may be marked as empty. In step 803, if the answer is yes, a module or other hardware and/or software component considers whether the defined space yields informative data about the sample nucleic acids. In step 804, if the answer is no, the defined space may be marked as non-informative. In step 805, if the answer is yes, a module or other hardware and/or software component considers whether the sample nucleic acid(s) correspond to one of a test fragment (TF) and a library fragment (LF). In step 806, if the answer is no, the defined space may be marked as ambiguous. In step 807, if the answer is yes, the defined space may be marked as TF or LF as the case may be.

In an exemplary embodiment, a sequencing key can be viewed as a unique identifier, such as a bar code, of the type or origin of the sample nucleic acid template or population of nucleic acid fragments to permit appropriate sorting and/or association of nucleic acid sequences randomly dispersed in an array. One, two, or more sequencing keys may be used. A "library sequencing key" or "library fragment key," for example, may be a known artificial nucleic acid sequence identified or associated with a fragment of a nucleic acid sequence from a library. The library sequencing key may be associated with or be part of an adapter sequence or have another association with particles including fragments from the library of a nucleic acid sequence of interest. A "test fragment sequencing key" or "test fragment key," for example, may be a known artificial nucleic acid sequence identified or associated with a known fragment of a nucleic acid used as a control or reference. If the library sequencing key and the test fragment sequencing key are distinct identifiers of each key, then a comparison of a read of unknown origin against each of them should produce a match or a comparison of sufficient confidence. If such identification cannot be made, then the information from that well can be flagged, discarded, or ignored as being an ambiguous well. The sequencing keys may have the same length or different lengths, in which case comparison may be based on the shortest length. Of course, other kinds of sequencing keys are possible, and a test fragment key may or may not always be used.

Figure 9:
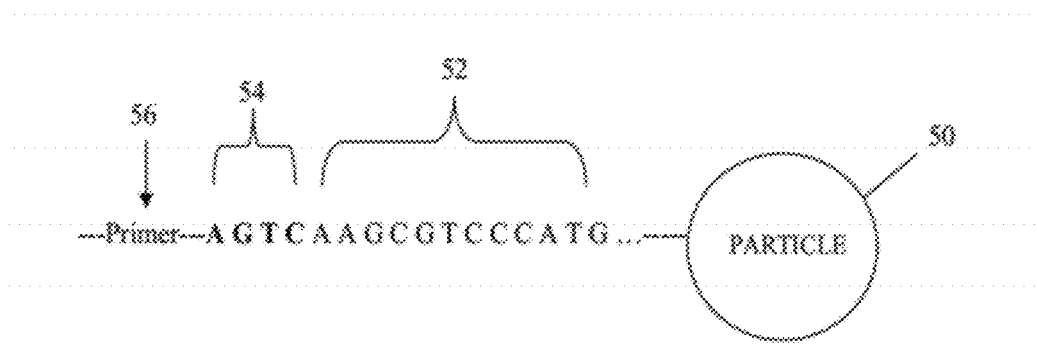
FIG. 9 illustrates a particle associated with a sample nucleic acid template, a primer, and a sequencing key according to an exemplary embodiment.

FIG. 9 illustrates a particle 50 associated with a sample nucleic acid template 52, a primer 56, and a sequencing key 54 according to an exemplary embodiment. The sequencing key (bold nucleotides A G T C), which may be added to the 5' end of the sample nucleic acid template to be at the beginning of a read to permit early identification and classification of the origin of the sample nucleic acid template (as a test fragment or a library fragment, for example). If no identification can be made (e.g., where there is no or low signal strength, ambiguous identification of the sample nucleic acid template, and/or a particle with more than one type of sample nucleic acid template or fragment (e.g., polyclonal)), the fragment may be classified as being ambiguous. A particle could have multiple sequencing keys for classifying different aspects. For example, one such key might be used to determine whether a sample is a library fragment, and another (which could have a different length (e.g., longer)) might be used to serve as an additional "bar code" for the sample.

A comparison of a read of unknown origin against a sequencing key may be done in various ways depending on the format of the signals at the time of classification. The comparison may be done in "base-space" format (e.g., using a series or vector of nucleotide designations such as A, C, G, and T that correspond to the series of nucleotide species that were flowed and incorporated). The comparison may also be done in "flow-space" format (e.g., using a series or vector of zeros and ones representing a non-incorporation event (a zero, "0") for a given nucleotide flow or a nucleotide incorporation event (a one, "1") for a given nucleotide flow). Thus, in flow-space format, the nucleotide flow order and whether and how many non-events and events occurred for any given nucleotide flow determine the flow-space format series of zeros and ones, which may be referred to as the flow order vector. (Of course, zeros and ones are merely convenient representations of a non-incorporation event and a nucleotide incorporation event, and any other symbol or designation could be used alternatively to represent and/or identify such non-events and events.) Also, in some exemplary embodiments, a homopolymer region may be represented by a whole number greater than one, rather than the respective number of one's in series (e.g., one might opt to represent a "T" flow resulting in an incorporation followed by an "A" flow resulting in two incorporations by "12" rather than "111" in flow-space).

To illustrate the interplay between base-space vectors, flow-space vectors, and nucleotide flow orders, one may consider, for example, an underlying template sequence beginning with "TA" subjected to multiple cycles of a nucleotide flow order of "TACG." The first flow, "T," would result in a non-incorporation because it is not complementary to the template's first base, "T." In the base-space vector, no nucleotide designation would be inserted; in the flow-space vector, a "0" would be inserted, leading to "0." The second flow, "A," would result in an incorporation because it is complementary to the template's first base, "T." In the base-space vector, an "A" would be inserted, leading to "A"; in the flow-space vector, a "1" would be inserted, leading to "01." The third flow, "C," would result in a non-incorporation because it is not complementary to the template's second base, "A." In the base-space vector, no nucleotide designation would be inserted; in the flow-space vector, a "0" would be inserted, leading to "010." The fourth flow, "G," would result in a non-incorporation because it is not complementary to the template's second base, "A." In the base-space vector, no nucleotide designation would be inserted; in the flow-space vector, a "0" would be inserted, leading to "0100." The fifth flow, "T," would result in an incorporation because it is complementary to the template's second base, "A." In the base-space vector, a "T" would be inserted, leading to "AT"; in the flow-space vector, a "1" would be inserted, leading to "01001." (Note: if the analysis were to contemplate a potentially longer template, an "X" could be inserted here instead because additional "A's" could potentially be present in the template in the case of a longer homopolymer, which would allow for more than one incorporations during the fifth flow, leading to "0100X.") The base-space vector thus shows only the sequence of incorporated nucleotides, whereas the flow-space vector shows more expressly the incorporation status corresponding to each flow. Whereas a base-space representation may be fixed and remain common for various flow orders, the flow-based representation depends on the particular flow order. Knowing the nucleotide flow order, one can infer either vector from the other. Of course, the base-space vector could be represented using complementary bases rather than the incorporated bases (thus, one could just as well define the base-space representation of a sequencing key as being the incorporated nucleotides or as being the complementary nucleotides of the template against which the flowed nucleotides would be incorporated).

Table 1 shows exemplary library and test fragment sequencing keys in both base-space format and in flow-space format for a nucleotide flow order of TACG.

TABLE 1

|  | Base-space format | Flow-space format |
| --- | --- | --- |
| Library Fragment Sequencing Key | TCAG | 1010010X |
| Test Fragment Sequencing Key | ATCG | 0100101X |

Figure 10:
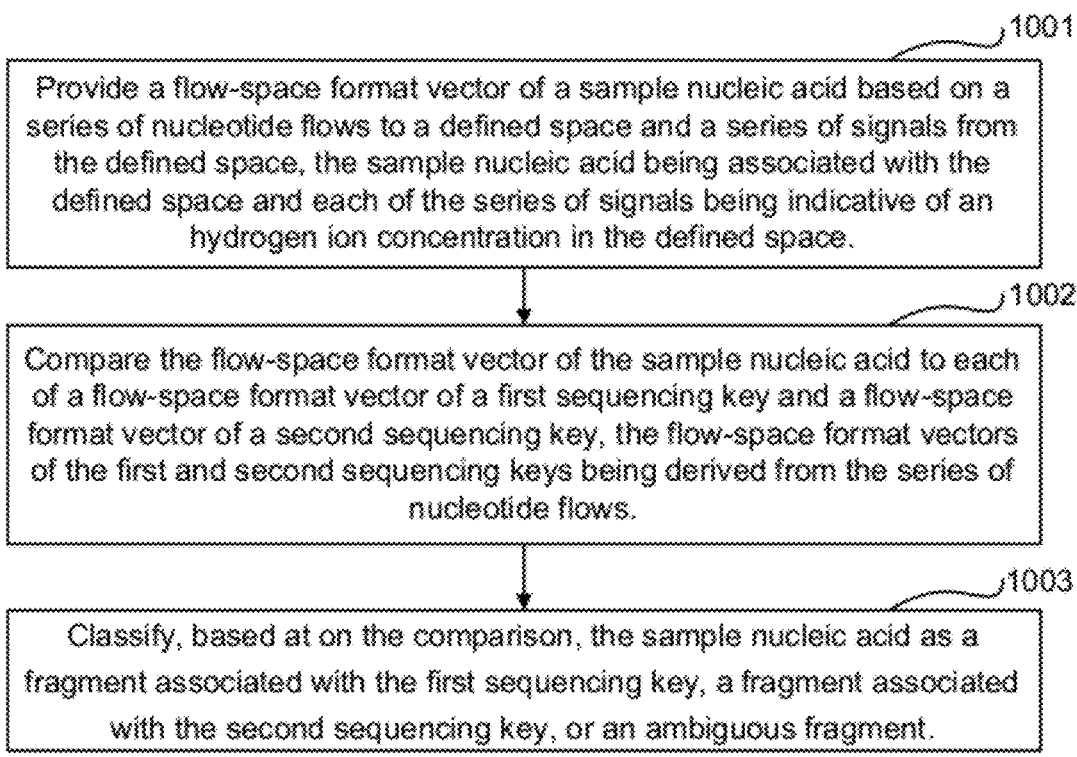
FIG. 10 illustrates a method for classifying a content of a defined space according to an exemplary embodiment.

FIG. 10 illustrates a method for classifying a content of a defined space according to an exemplary embodiment. In step 1001, a module or other hardware and/or software component provides a flow-space format vector of a sample nucleic acid based on a series of nucleotide flows to a defined space and a series of signals from the defined space, the sample nucleic acid being associated with the defined space and each of the series of signals being indicative of the hydrogen ion concentration in the defined space. In step 1002, a module or other hardware and/or software component compares the flow-space format vector of the sample nucleic acid to each of a flow-space format vector of a first sequencing key and a flow-space format vector of a second sequencing key, the flow-space format vectors of the first and second sequencing keys being derived from the series of nucleotide flows. In step 1003, a module or other hardware and/or software component classifies, based on the comparison, the sample nucleic acid as a fragment associated with the first sequencing key, a fragment associated with the second sequencing key, or an ambiguous fragment.

According to an exemplary embodiment, there is provided a method for classifying a content of a defined space, including: (1) providing a flow-space format vector of a sample nucleic acid based on a series of nucleotide flows to a defined space and a series of signals from the defined space, the sample nucleic acid being associated with the defined space and each of the series of signals being indicative of the hydrogen ion concentration in the defined space; (2) comparing the flow-space format vector of the sample nucleic acid to each of a flow-space format vector of a first sequencing key and a flow-space format vector of a second sequencing key, the flow-space format vectors of the first and second sequencing keys being derived from the series of nucleotide flows; and (3) classifying, based on the comparison, the sample nucleic acid as a fragment associated with the first sequencing key, a fragment associated with the second sequencing key, or an ambiguous fragment. In such a method, providing a flow-space format vector may include determining for a first nucleotide flow of the series of nucleotide flows of a first nucleotide whether a 0-mer, a 1-mer, a 2-mer, a 3-mer, a 4-mer, or a higher order number of nucleotide incorporation events occurred based on the signal from the defined space associated with the first nucleotide flow, wherein a 0-mer nucleotide incorporation event is a non-incorporation event. Providing a flow-space format vector of a sample nucleic acid may include recording sequentially, as the flow-space format vector of the sample nucleic acid: 0, 1, 11, 111, or 1111, or the higher order number of ones (1's) for a corresponding 0-mer, 1-mer, 2-mer, 3-mer, 4-mer, or the higher order number nucleotide incorporation events, respectively. Providing a flow-space format vector of a sample nucleic acid may further include repeating the determining and recording for a second nucleotide flow of a second nucleotide, for a third nucleotide flow of a third nucleotide, and for a fourth nucleotide flow of a fourth nucleotide. Providing a flow-space format vector of a sample nucleic acid may further include repeating the determining and recording for a fifth nucleotide flow of the first nucleotide, for a sixth nucleotide flow of the second nucleotide, for a seventh nucleotide flow of the third nucleotide, and for an eighth nucleotide flow of the fourth nucleotide, and so on until at least one nucleotide incorporation event occurs for each of the four nucleotides. The first sequencing key may include a library sequencing key and the second sequencing key may include a test fragment sequencing key. According to an exemplary embodiment, there is provided a non-transitory machine-readable storage medium comprising instructions which, when executed by a processor, cause the processor to perform such a method for classifying a content of a defined space or related methods and variants thereof.

In an exemplary embodiment, sequencing keys may be designed in a principled manner by increasing a likelihood that they will be sufficiently distinguishable so that the identification can be made with sufficient confidence. For a pair of sequencing keys, such design may be done by evaluating an orthogonality (or distinctiveness) between the keys. Sequencing keys may be orthogonal with respect to zero, one, two, three, or four nucleotides, with a higher number signifying a higher separation between the keys, which may result in increased confidence in the accuracy of the identification of the origin of the read of the sample nucleic acid, and which can allow identification and classification using fewer bases/flows (and thus less data). As shown in several detailed examples below, which are explanatory only and not to be construed as limiting or restrictive in any way, two sequencing keys can be considered to be orthogonal with respect to a given nucleotide if two conditions or rules are satisfied for the given nucleotide in flow-space. The rules are as follows:

Rule 1: Both a non-incorporation event ("0-mer") and a nucleotide incorporation event ("1-mer") must be present in each sequencing key for the given nucleotide.

Rule 2: Each nucleotide incorporation event ("1-mer") or non-incorporation event ("0-mer") in one sequencing key for any given flow of the given nucleotide must correspond to an opposite non-incorporation event ("0-mer") or nucleotide incorporation event ("1-mer") in the other sequencing key.

EXAMPLE 1

As a first example, one may consider the orthogonality of the sequencing keys set forth above in Table 1 for nucleotide flow order TACG. The flow-space format vectors are reproduced below (without the "X," which is an unknown). Each row represents a sequencing key and each column represents a nucleotide flow. As explained below, these keys may be considered orthogonal with respect to T, A, and C, but not G.

| 1 | 0 | 1 | 0 | 0 | 1 | 0 |
|---|---|---|---|---|---|---|
| 0 | 1 | 0 | 0 | 1 | 0 | 1 |

Regarding the "T" nucleotide, which corresponds to the first and fifth flows (see bolded columns below), each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "T."

| 1 | 0 | 1 | 0 | 0 | 1 | 0 |
|---|---|---|---|---|---|---|
| 0 | 1 | 0 | 0 | 1 | 0 | 1 |

Regarding the "A" nucleotide, which corresponds to the second and sixth flows, each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "A."

| 1 | 0 | 1 | 0 | 0 | 1 | 0 |
|---|---|---|---|---|---|---|
| 0 | 1 | 0 | 0 | 1 | 0 | 1 |

Regarding the "C" nucleotide, which corresponds to the third and seventh flows, each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "C."

| 1 | 0 | 1 | 0 | 0 | 1 | 0 |
|---|---|---|---|---|---|---|
| 0 | 1 | 0 | 0 | 1 | 0 | 1 |

Finally, regarding the "G" nucleotide, which corresponds to the fourth flow, each key does not include both a nucleotide incorporation event ("1") and a non-incorporation event ("0"), thereby failing to meet rule 1. Thus, these keys may not be considered orthogonal with respect to "G."

| 1 | 0 | 1 | 0 | 0 | 1 | 0 |
|---|---|---|---|---|---|---|
| 0 | 1 | 0 | 0 | 1 | 0 | 1 |

EXAMPLE 2

As a second example, one may consider the orthogonality of an alternative library sequencing key (CTAGT) with the same test fragment sequencing key set forth above in Table 1 for nucleotide flow order TACG. The flow-space format vectors are reproduced below. Each row represents a sequencing key and each column represents a nucleotide flow.

| 0 | 0 | 1 | 0 | 1 | 1 | 0 | 1 | X |
|---|---|---|---|---|---|---|---|---|
| 0 | 1 | 0 | 0 | 1 | 0 | 1 | X | |

Because the two vectors here have different lengths, comparison may be based on the first seven known values. As explained below, these keys may be considered orthogonal with respect to A and C, but not G and T.

| 0 | 0 | 1 | 0 | 1 | 1 | 0 |
|---|---|---|---|---|---|---|
| 0 | 1 | 0 | 0 | 1 | 0 | 1 |

Regarding the "T" nucleotide, which corresponds to the first and fifth flows, each key includes both a nucleotide incorporation event ("1") and a non-incorporation event ("0"), thereby meeting rule 1, however, each nucleotide incorporation event or non-incorporation event (i.e., "1" or "0") in one key corresponds to an identical nucleotide incorporation event or non-incorporation event (i.e., "1" or "0") in the other key, thereby failing to meet rule 2. Thus, these keys may not be considered orthogonal with respect to "T."

| 0 | 0 | 1 | 0 | 1 | 1 | 0 |
|---|---|---|---|---|---|---|
| 0 | 1 | 0 | 0 | 1 | 0 | 1 |

Regarding the "A" nucleotide, which corresponds to the second and sixth flows, each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "A."

| 0 | 0 | 1 | 0 | 1 | 1 | 0 |
|---|---|---|---|---|---|---|
| 0 | 1 | 0 | 0 | 1 | 0 | 1 |

Regarding the "C" nucleotide, which corresponds to the third and seventh flows, each key includes both a nucleotide incorporation event ("1") and a non-incorporation event ("0"), thereby meeting rule 1, and each nucleotide incorporation event or non-incorporation event (i.e., "1" or "0") in one key corresponds to an opposite non-incorporation event or nucleotide incorporation event (i.e., "0" or "1") in the other key, thereby meeting rule 2. Thus, these keys may be considered orthogonal with respect to "C."

| 0 | 0 | 1 | 0 | 1 | 1 | 0 |
|---|---|---|---|---|---|---|
| 0 | 1 | 0 | 0 | 1 | 0 | 1 |

Finally, regarding the "G" nucleotide, which corresponds to the fourth flow, each key does not include both a nucleotide incorporation event ("1") and a non-incorporation event ("0"), thereby failing to meet rule 1. Thus, these keys may not be considered orthogonal with respect to "G."

| 0 | 0 | 1 | 0 | 1 | 1 | 0 |
|---|---|---|---|---|---|---|
| 0 | 1 | 0 | 0 | 1 | 0 | 1 |

Figure 11:
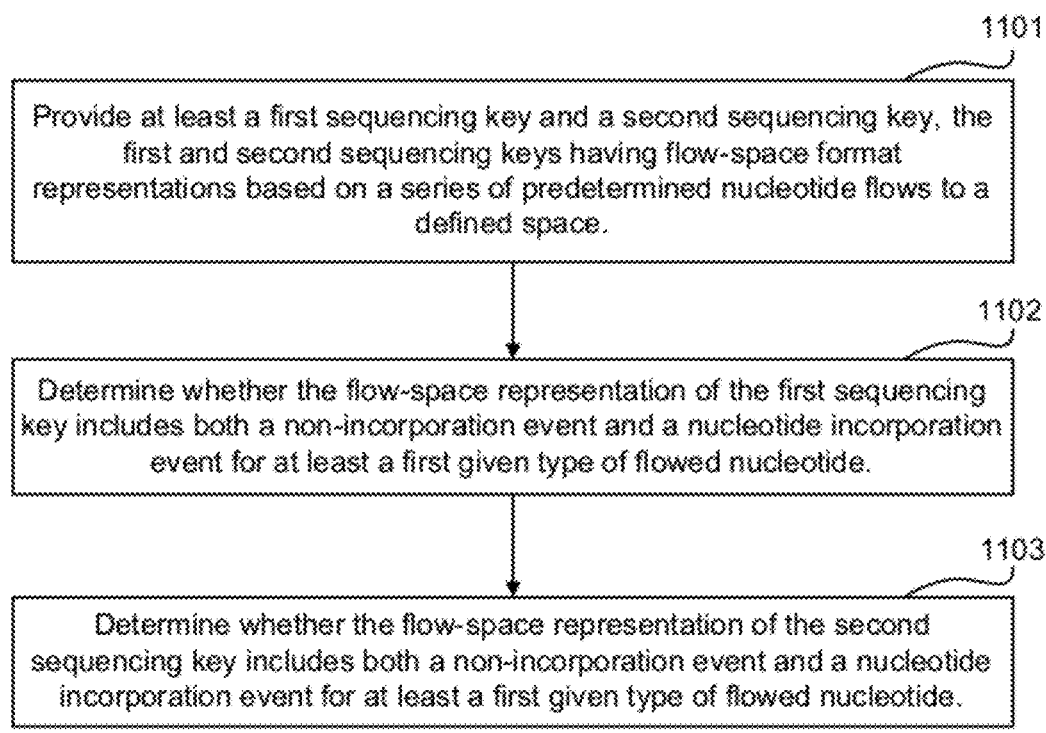
FIG. 11 illustrates a method for selecting sequencing keys according to an exemplary embodiment.

FIG. 11 illustrates a method for selecting sequencing keys according to an exemplary embodiment. In step 1101, a module or other hardware and/or software component provides at least a first sequencing key and a second sequencing key, the first and second sequencing keys having flow-space format representations based on a series of predetermined nucleotide flows to a defined space. In step 1102, a module or other hardware and/or software component determines whether the flow-space format representation of the first sequencing key includes both a non-incorporation event and a nucleotide incorporation event for at least a first given type of flowed nucleotide. In step 1103, a module or other hardware and/or software component determines whether the flow-space format representation of the second sequencing key includes both a non-incorporation event and a nucleotide incorporation event for at least the first given type of flowed nucleotide.

According to an exemplary embodiment, there is provided a method for selecting sequencing keys, including: (1) providing at least a first sequencing key and a second sequencing key, the first and second sequencing keys having flow-space format representations based on a series of predetermined nucleotide flows to a defined space; (2) determining whether the flow-space format representation of the first sequencing key includes both a non-incorporation event and a nucleotide incorporation event for at least a first given type of flowed nucleotide; and (3) determining whether the flow-space format representation of the second sequencing key includes both a non-incorporation event and a nucleotide incorporation event for at least the first given type of flowed nucleotide. In such a method, the defined space may be configured to generate a series of signals indicative of an hydrogen ion concentration in the defined space. The method may further include determining for at least the first given type of flowed nucleotide whether each nucleotide incorporation event or non-incorporation event in the flow-space format representation of the first sequencing key for any given flow of the at least first given type of flowed nucleotide corresponds to an opposite non-incorporation event or nucleotide incorporation event in the flow-space format representations of the second sequencing key. The method may further include concluding, if each of the determining steps results in a positive response, that the first sequencing key and the second sequencing key are orthogonal with respect to the at least first given type of flowed nucleotide. The method may further include repeating one or more of the determining steps for a second given type of flowed nucleotide, a third given type of flowed nucleotide, and a fourth given type of flowed nucleotide to determine whether the first sequencing key and the second sequencing key are orthogonal with respect to one or more of the second given type of flowed nucleotide, the third given type of flowed nucleotide, and the fourth given type of flowed nucleotide. The first sequencing key may include a library sequencing key and the second sequencing key may include a test fragment sequencing key. The method may include determining, for the first occurrence of a first nucleotide in the first sequencing key, whether a single incorporation event in the first sequencing key occurs during a non-incorporation event for the second sequencing key for the same nucleotide flow; and determining, for the first occurrence of the first nucleotide in the second sequencing key, whether a single incorporation event in the second sequencing key occurs during a non-incorporation event for the first sequencing key for the same nucleotide flow. According to an exemplary embodiment, there is provided a non-transitory machine-readable storage medium comprising instructions which, when executed by a processor, cause the processor to perform such a method for selecting sequencing keys or related methods and variants thereof.

According to an exemplary embodiment, there is provided a system for nucleic acid sequencing, including: (1) a vector comparison module configured to compare a flow-space format vector of a sample nucleic acid to a flow-space format vector of a first sequencing key and a flow-space format vector of a second sequencing key, wherein the first and second sequencing keys are derived from a series of nucleotide flows; and (2) a nucleic acid origin identification module configured to identify, based on the comparison, the sample nucleic acid as being associated with the first sequencing key, the second sequencing key, or as an ambiguous fragment.

Figure 12:
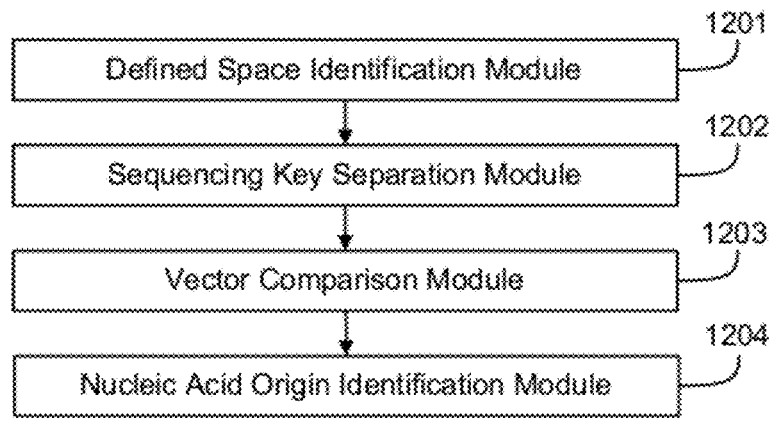
FIG. 12 illustrates components of a classification module according to an exemplary embodiment.

FIG. 12 illustrates components of a classification module according to an exemplary embodiment. The classification module includes a defined space identification module 1201 for determining whether a defined space includes a particle and/or sample nucleic acid template and whether it provides useful data, for example; a sequencing key separation module 1202 for evaluating and determining a degree of separation or an orthogonality of a pair of sequencing keys or bar codes; a vector comparison module 1203 for comparing a flow-space format vector of a sample nucleic acid template to a flow-space format vector of a first sequencing key and a flow-space format vector of a second sequencing key, where the first and second sequencing keys are derived from a series of nucleotide flows; and a nucleic acid origin identification module 1204 for identifying and/or classifying, based on the comparison, the sample nucleic acid template as being associated with the first sequencing key, associated with the second sequencing key, or as an ambiguous fragment. These modules can process data from defined spaces to evaluate, identify, flag, and/or exclude non-informative data while keeping useful data for further processing.

Figure 13:
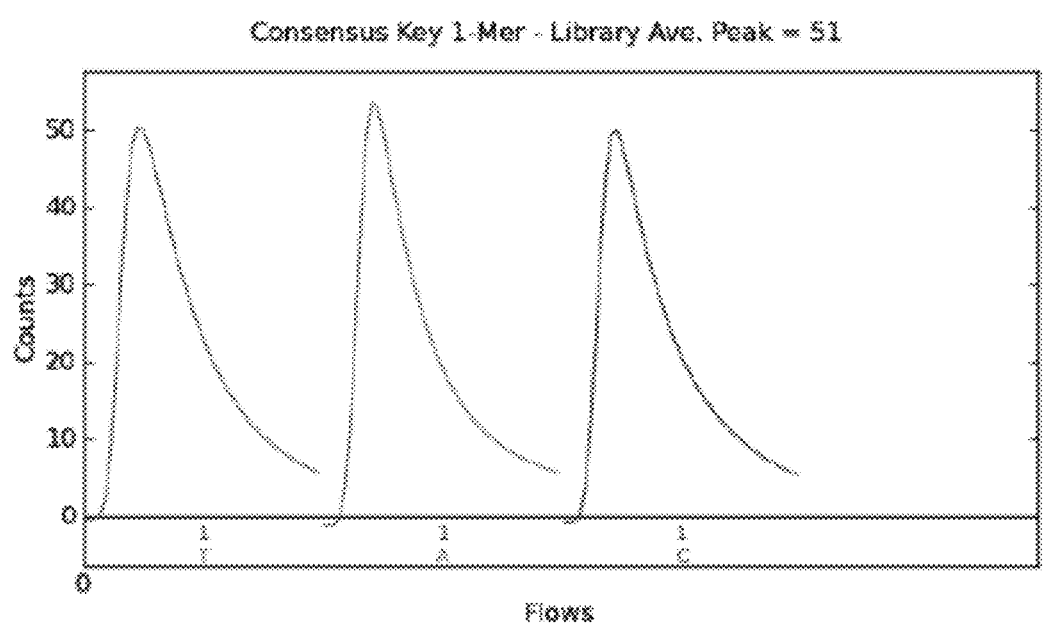
FIG. 13 illustrates consensus incorporation signals for three initial bases of a library sequencing key according to an exemplary embodiment.

FIG. 13 illustrates consensus incorporation signals averaged from a large number of reads for three initial bases of a library sequencing key according to an exemplary embodiment. The consensus incorporation signals may be used by a user to visually confirm the quality of a run, for example.

Figure 14A:
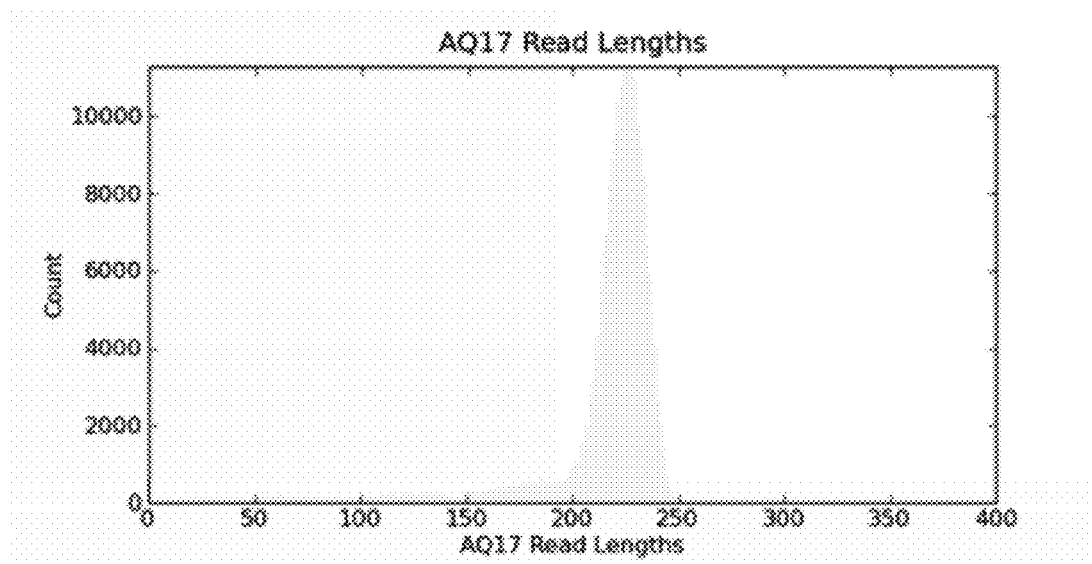
FIG. 14A illustrates a histogram of library read lengths according to an exemplary embodiment.

FIG. 14A illustrates a histogram of library read lengths according to an exemplary embodiment. The histogram depicts the AQ17 read length for each read aligned to a reference genome.

Figure 14B:
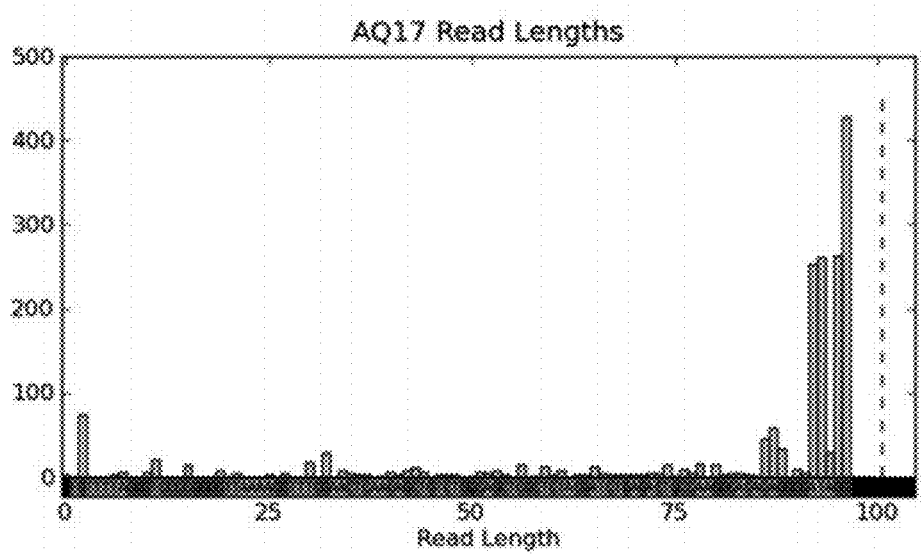
FIG. 14B illustrates a histogram of test fragment read lengths according to an exemplary embodiment.

FIG. 14B illustrates a histogram of test fragment read lengths according to an exemplary embodiment. The histogram depicts the AQ17 read length of each test fragment as mapped to its reference (actual) sequence. The distribution of test fragment lengths is highly concentrated because test fragments are positive controls of known composition and defined length.

In an exemplary embodiment, the classification module may receive directly or indirectly a data file, e.g., from the data processing module, and may store, transmit, or output classification information in a MASK file format (e.g., bfmask.bin), which can contain one or more bit flags for each well, indicating the contents of each defined space.

Signal Processing Module

In an exemplary embodiment, a signal processing module or signal processor may be configured to analyze signal information from a defined space or reaction confinement region and an associated sample nucleic acid template. The signal processing module may output a processed signal, which may be considered a raw incorporation signal. The signal processing module may use information and data resulting from the classification module and associated methods, but may also use raw data or raw signals.

In an exemplary embodiment, the signal processing module may be configured to remove noise from raw signal and improve a quality of the signal, which may include an accuracy and a signal-to-noise ratio of the raw signals, for example. Noise, which may be due to various causes including thermal sensitivity of the sensors, electrical potential disturbances in the fluid (such as resistive or thermal noise in the fluids, reference voltage changes due to different fluids contacting the reference electrode), pH changes due to bulk changes in fluids that are passed over the sensor array (referred to herein as "reagent change noise"), stochastic behavior of polymerase function (e.g., incomplete extensions) or failure to completely wash away all dNTPs in a given step (e.g., inappropriate incorporation), for example, may be removed in various ways.

In an exemplary embodiment, the signal processing module may be configured to remove from the data and signals it received some background signal or noise to generate an improved incorporation signal. To minimize computation time, the signal processing module may only process data and signals for defined spaces containing particles and/or having produced a sufficiently strong signal to indicate a nucleotide incorporation event. The background or noise portion of the signal can be present during each flow and can vary over time, across an array of wells, and during an acquisition.

In an exemplary embodiment, the signal processing module may be configured to create an incorporation fitting model, which may have two parts. The first part may include determining the background signal that would have been measured in a given defined space had no nucleotide incorporation event occurred. The second part may include subtracting or otherwise removing (or fitting) the background signal from the raw signal and then examining and analyzing (or fitting) the signal that remains. The result of the incorporation fitting model may be an estimate of incorporation during each nucleotide flow for each well.

In an exemplary embodiment, the signal processing module may be configured to perform or implement one or more of the teachings disclosed in Rearick et al., U.S. Pat. appl. Ser. No. 13/339,846, titled "Models for Analyzing Data From Sequencing-by-Synthesis Operations", filed Dec. 29, 2011, based on U.S. Prov. Pat. Appl. Nos. 61/428,743, filed Dec. 30, 2010, and 61/429,328, filed Jan. 3, 2011, and in Hubbell, U.S. Pat. appl. Ser. No. 13/339,753, titled "Time-Warped Background Signal for Sequencing-by-Synthesis Operations", filed Dec. 29, 2011, based on U.S. Prov. Pat. Appl. No. 61/428,097, filed Dec. 29, 2010, which are all incorporated by reference herein in their entirety.

In an exemplary embodiment, the signal processing module may receive a MASK file from the classification module, for example. The signal processing module may store, transmit, and/or output raw incorporation signals and related information and data in raw WELLS file format, for example. The signal processing module may output a raw incorporation signal per defined space and per flow, for example.

Base Caller Module

In an exemplary embodiment, a base caller module or base caller may be configured to transform a raw incorporation signal into a base call and compile consecutive base calls associated with a sample nucleic acid template into a read. A base call refers to a particular nucleotide identification (e.g., dATP ("A"), dCTP ("C"), dGTP ("G"), or dTTP ("T")). The base caller module may perform one or more signal normalizations, signal phase and signal droop (e.g, enzyme efficiency loss) estimations, and signal corrections, and it may identify or estimate base calls for each flow for each defined space. The base caller module may share, transmit or output non-incorporation events as well as incorporation events.

In an exemplary embodiment, the base caller module may be configured to normalize a read, which may include initially using raw data and/or signals from the signal processing module. For example, using one or more known expected 1-mer events, which may be identified using sequencing keys, a 1-mer average signal may initially be established and used for normalization. Then, as the base caller module processes each defined space, additional base calls can be accurately determined and additional measurements then can be used to re-normalize the raw signals. Such re-normalization process may improve confidence (e.g., a higher signal-to-noise ratio) of the signal from each defined space.

In an exemplary embodiment, the base caller module may be configured to observe and account for signal droop that in some instances may be attributed to DNA polymerase loss that can occur during a sequencing run. Such DNA polymerase loss may be experienced during nucleotide incorporation events, with values typically in the range of about 0.1% to about 0.2% over the course of a run. By averaging groups of reads in a region together and/or averaging their signals after normalization, an exponential can be fit to the resulting curve, from which the rate of signal loss over time can be extracted to determine an estimate of the DNA polymerase loss during nucleotide incorporation events.

In an exemplary embodiment, the base caller module may be configured to use the signal droop in a signal phase model as a constant for a read. Signal estimates can vary across an array of defined spaces, but signal droop estimates often can be assumed to be fixed for each processed region. The signal phase model can fit parameters, including carry-forward and incomplete extension parameters, which may lead to an estimate of the carry-forward and incomplete extension for each defined space. The resulting values may be averaged over small regions to reduce errors and noise in the fit. The output carry-forward and incomplete extension values can be used as inputs to other parts of the base caller module, for example, a solver function.

In an exemplary embodiment, the base caller module may include a solver function that can apply phase and droop estimates to the normalized signals and make predictions of the likely signal measurements for each nucleotide flow for probable nucleotide incorporation events. The solver function can compare the actual measured value to a list of predicted values and the best fit prediction at each nucleotide flow can be used as the base call for that flow. For example, a 0-mer, 1-mer, 2-mer, 3-mer, 4-mer, and higher order nucleotide incorporations can be predicted at each nucleotide flow. The solver function can continue such processing over the entire read. At the end of one pass, a good estimate of all base calls for that read can be made. The solver function then can iterate over the read again, applying the same phase and droop estimates at each nucleotide flow, to refine the base calls.

In an exemplary embodiment, the base caller module may be configured to perform or implement one or more of the teachings disclosed in Davey et al., U.S. Pat. Appl. No. 13/283,320, filed Oct. 27, 2011, based on U.S. Prov. Pat. Appl. No. 61/407,377, filed on Oct. 27, 2010, which are both incorporated by reference herein in their entirety.

In an exemplary embodiment, the base caller module may receive data in WELLS file format. The base caller module may store, transmit, and/or output reads and related information in a standard flowgram format ("SFF"), for example.

Read Filter Module

In an exemplary embodiment, a read filter module or read filter may be configured to generate quality metrics for each base call of a read and for each read of a set of reads. For example, adapter sequences or other low quality base calls may be trimmed out. Low quality base calls may be removed from the output data by filtering out entire reads and/or trimming low quality 3' ends of reads using various filters and protocols.

Quality Scoring:

In an exemplary embodiment, the read filter module may be configured to assign per-base quality scores to each read, and the per-base quality scores can be written to an SFF file along with the read itself. The per-base quality scores can be assigned by calculating metrics for the read, which metrics may be analyzed by comparison to a pre-defined quality lookup table, which may be a phred-like table established through prior system training. (Phred quality scores, which were created by the program phred to aid in sequencing nucleic acid (DNA) in the Human Genome Project, can characterize the quality of a DNA sequence.) A phred quality score Q may be defined as a property that is logarithmically related to a base-calling error probability P, such that $Q=-10 \log P$ or equivalently $P=10^{(-Q/10)}$. Thus, when referring to a Q20 assigned to a specific base, for example, it is meant that a base with Q20 has a 0.99 probability of being correct. The metrics may include estimates of accuracy of the current base call, nucleotide flow, and earlier or later base calls or nucleotide flows for each read. The quality scores may be based on nucleotide flow values for each base, from which several quality predictors can be calculated. The quality look-up table may be generated by selecting a representative data set to use as a training set, which may use a variety of quality predictors to characterize the quality of a base call. See Brockman et al., Genome Research 18:763-770 (2008), which is incorporated by reference herein in its entirety. In an exemplary embodiment, the read filter module may be configured to use quality predictors, which may include base position, local noise, read noise, multiple incorporations, phase error, and environment noise, for example, as part of an index to look-up an appropriate quality score for the base call in phred-like quality look-up table.

In an exemplary embodiment, the base position quality predictor may be the base position in the read from the start of the nucleic acid sequence. The local noise quality predictor may be the noise in an immediate neighborhood of a given base, which neighborhood may be varied depending on the particulars of the application and run (e.g., the local noise quality predictor may be defined to be within plus or minus (±) one base of the given base, or within ±2 bases of the given base, for example. The read noise quality predictor may be a peak-normalized expression of the mean and the standard deviation of all 0-mers and 1-mers of a read. The multiple incorporations quality predictor may, in the case of multiple incorporations of the same nucleotide in one nucleotide flow (a homopolymer region), assign to the last base in the homopolymer region a value equivalent to the total number of incorporations during that particular nucleotide flow (while all other bases in the homopolymer region can be assigned a value of 1). The phase error quality predictor may be the number of incorporations of the same nucleotide in the previous nucleotide flow. The environment noise quality predictor may be the noise in a larger neighborhood of a given base, the area of which neighborhood may vary depending on the application and run (e.g., the environmental noise quality predictor may be in a larger neighborhood which is defined to be within ±10 bases of the given base, or within ±5 bases, ±6 bases, ±7 bases, ±8 bases, ±9 bases, ±11 bases, ±12 bases, or more, for example. In an exemplary embodiment, the quality predictors may include a phase error combined with one or more of base position, local noise, read noise, multiple incorporations, and environment noise.

In an exemplary embodiment, after a quality look-up table has been generated, the quality look-up table may be used to assign a per base quality score independent of alignment. For example, quality predictors can be calculated for each base of a sample nucleic acid sequence template. The corresponding per base quality score may be determined by locating, in the quality look-up table, the first line for which the six above-mentioned calculated quality predictors, for example, are less than or equal to the quality predictor values in the quality look-up table. The quality score then can be read from the same line.

Filtering Reads:

In an exemplary embodiment, the read filter module may be configured to calculate an overall quality metric representing the base caller module's ability to correct accurately and base call the raw signal measurements. Low quality reads can be mixed reads or very low copy-count reads that produce low quality nucleic acid sequences such that they do not fit an expected incorporation model, for example. Reads identified as low quality typically may be excluded and not written to the SFF or FASTQ file.

Various types of filtering may occur. For example, reads that are derived from wells with non-clonal nucleic acid template populations and/or that are generally a poor fit to the base calling model's expectations for high quality data may be targeted for removal, whether because of low or poor signal quality from the well or a low copy count of sample nucleic acid templates. Specifically, particles or wells identified to non-clonal nucleic acids typically are filtered from the data as they contain a mixture of different nucleic acid templates (which may result from nucleic acid templates that are amplified on a single particle but are derived from multiple, different input nucleic acid templates).

A mixed nucleic acid template read can occur because of the presence of two or more distinct nucleic acid fragments in a vesicle or droplet at the start of an emulsion PCR stage, for example, or because of the collapsing together of different emulsion vesicles or droplets. Regardless of origin, mixed nucleic acid template reads can be identified by searching for reads in which an unusually large proportion of nucleotide flows are estimated to result in a nucleotide incorporation event. For example, when no mixed nucleic acid template reads exist, each particle will have a single sample nucleic acid template species amplified onto it. Based on a four-nucleobase flow cycle and uniform and random nucleotide content in the sample nucleic acid sequence template, sequencing of such a sample nucleic acid template is expected to result in approximately one-half (50%) of the nucleotide flows having a positive nucleotide incorporation event. By contrast, when a particle contains multiple different sample nucleic acid templates, or mixed nucleic acid template reads, the number of nucleotide flows with a positive nucleotide incorporation event signal can be expected to increase substantially.

In an exemplary embodiment, the read filter module may be configured to filter based on a percentage of positive flows ("PPF"). The PPF (percentage of positive nucleotide incorporation events based on the total number of nucleotide flows) may be evaluated over a given number of nucleotide flows, for example, the first 30 nucleotide flows, the first 40 nucleotide flows, the first 60 nucleotide flows, or the first 75 nucleotide flows, for example. Subsequently, a PPF threshold can be set to exclude reads having a PPF greater than a threshold value. For example, if the PPF value is greater than about 60%, or greater than about 65% or greater than about 70%, the read can be excluded from the set of reads for further analysis, for example, alignment, and/or before writing out to an SFF or FASTQ file. If a particular read does not have the minimum number of nucleotide flows to meet the nucleotide flow number threshold, the actual number of nucleotide flows may be used to calculate the PPF and determine whether to filter the read. In addition, certain reads that have a PPF below an expected value may be filtered out. Thus, in various exemplary embodiments, a read may be identified as acceptable if it has a PPF between about 40% to about 60%, between about 45% to about 55%, between about 35% to about 65%, or between about 30% to about 70%, for example, including various combinations of upper and lower thresholds as dictated by the particular application and run.

In an exemplary embodiment, the read filter module may be configured to filter based on a PPF, while taking account of the fact that test fragments can be excluded from read filtering based on the PPF because test fragment sequences often are designed with sequences that typically do not occur naturally and therefore, can result in a large PPF. In an embodiment, such test fragments are identified but without filtering the corresponding reads from a set of filtered reads.

In an exemplary embodiment, the read filter module may be configured to filter from further processing certain possibly useful nucleic acid sequences using the PPF filter. For example, a long sample nucleic acid template which has a repeating sequence that is exactly the same as a nucleotide flow order would be expected to have a positive nucleotide incorporation event for every nucleotide flow (and, theoretically, a PPF of 100%). Because of the large PPF, the hypothetical, long sample nucleic acid template would be identified as a mixed nucleic acid template read and filtered. Although such a piece of information may be unused or under-utilized, in practice, such sequences should be very rare and the benefits of generally excluding low quality reads resulting from mixed nucleic acid templates based on a threshold PPF are favored over excluding a very small proportion of genuine reads.

In an exemplary embodiment, the read filter module may be configured to filter reads based on non-PPF criteria. For example, read filtering may include targeted removal of reads that are generally a poor fit to the base calling model's expectations for high quality data. A typical or "well-behaved" read can be modeled and will have certain expectations about its signal distribution. For example, after the amount of incomplete extension and carry forward phasing effects have been estimated, certain expectations are present for how signals in neighboring nucleotide flows should be elevated or depressed. For example, when a positive incomplete extension is in effect, a large homopolymer sequence should result in a depressed signal in the nucleotide flow corresponding to the homopolymer while an elevated signal should be present in the next nucleotide flow of the same nucleotide.

In an exemplary embodiment, the read filter module may be configured to filter reads based on a difference between an observed signal and an expected signal based on a prediction of a base calling model for each nucleotide flow for each read (which may be referred to as the flow residual for the well and nucleotide flow in question, e.g., flow residual equals observed signal minus predicted signal). In general, a high quality read which is well-described by the base calling model and the nucleic acid sequence that it estimates should have a low residual value. In an exemplary embodiment, the median absolute value of the flow residual values over a number of initial nucleotide flows may be tracked for each read as a measure of the agreement between the observed data and the base calling model. If the median absolute flow residual value of a read is greater than a predefined threshold, then the read may be considered unreliable and it may be filtered and excluded from further processing. In various exemplary embodiments, the median absolute flow residual value can be determined over the first 30 nucleotide flows, the first 40 nucleotide flows, the first 50 nucleotide flows, the first 60 nucleotide flows, or the first 70 nucleotide flows, for example. In various exemplary embodiments, if the median absolute flow residual value is above a threshold of about 0.1, about 0.12, about 0.13, about 0.15, or about 0.2, or greater, for example, the read may be filtered from the set of reads. For these criteria, a median absolute flow residual value filter can be applied to reads of both library fragments and test fragments.

Alternatively or in addition to the above, other characteristics of reads can be identified and evaluated to determine whether the read should be filtered as being of low quality. For example, the strength of the signal from a particular well can be evaluated over the first two, three, or four key nucleotides. A key nucleotide can be a nucleotide that is present in a library sequencing key or a test fragment sequencing key. Reads for wells that do not produce a strong signal across each of the predetermined number of (key) nucleotides may be filtered. Also, a read can be required to contain a minimum number (threshold) of base calls (nucleotides) to avoid identification as a low quality read. For example, a threshold read length can be at least 6 bases, at least 8 bases, at least 10 bases, at least 12 bases, at least 15 bases, at least 20 bases, or at least 25 bases, or more, for example. If a read does not contain the threshold read length, the read can be filtered from the set of reads for further processing. Further, in certain embodiments where sequencing keys are used, a read filter can require an exact match of a sequence of the read to the corresponding library sequencing key for that run. If an exact match is not identified, the read can be filtered.

Filtering or Trimming Base Calls:

In an exemplary embodiment, the read filter module may be configured to trim a read (e.g., by excising or removing one or more nucleotides (base calls) from the read) until an acceptable level of quality persists for the remaining portion of the read, rather than filtering a read in its entirety. A trimmed read may be used in further processing and/or written to a SFF or FASTQ file. For example, a read that contains an adapter sequence (e.g., a B-adapter) may be trimmed to remove the adapter sequence and other base calls determined to be of low quality. Searching a read for a match to a known adapter sequence may be done in flow-space using flow-space vectors. The effects of incomplete extension and carry forward phasing may be reversed to produce a phase-corrected ionogram (which can be stored in a SFF file). If a read extends into the adapter sequence, the 3' end of the phase-corrected ionogram can exhibit a pattern that is characteristic of the adapter sequence. In some embodiments, each position of the phase-corrected ionogram may be tested to determine whether it matches the pattern expected for the adapter sequence. Testing can include computing the Euclidean distance between the phase-corrected ionogram at the test position and the known ionogram for the adapter. If the distance falls below an adapter ionogram distance threshold, the corresponding position (translated from flow-space format back to base-space format) may be marked and/or recorded as an adapter trim location. If the distance does not fall below the adapter ionogram distance threshold, that position of the read does not match to the adapter sequence. In an embodiment, the adapter ionogram distance threshold may be a Euclidean distance of 5. In other embodiments, the adapter ionogram distance threshold may be a distance of 2, 3, 4, 6, 7, 8, 9, or more, for example.

Read trimming usually occurs at the 3' end of a read. However, in certain embodiments, base calls at the 5' end of a read can be trimmed, for example, where the base calls correspond to a sequencing key such as a library sequencing key. Considering the distribution of per base quality scores within a read, the highest quality base calls tend to occur at the start of the read, where phase errors typically are the smallest. The trimming of low quality base calls at the 3' end of a read may performed using a per base quality score threshold.

In various exemplary embodiments, base call trimming using a per base quality score may include scanning along the base calls of a read and computing a moving average in a fixed-length base call window along the read. A read trim point can be set to trim the earliest (5'-most) base call at which the moving average of the per base quality score drops below a moving average base quality score threshold. The base call window size may be 30 base calls and the moving average base quality score threshold, below which trimming will occur, may be a quality score of nine, for example. Of course, depending upon the particular run and application, the window size can be five base calls, 10 base calls, 15 base calls, 20 base calls, 25 base calls, 35 base calls, or 40 base calls, or more, for example. The moving average base quality score threshold also can vary depending on many factors and can be a quality score of 5, 6, 7, 8, 10, 11, 12, 13, 14, or 15, or more, for example.

As with other filters, each read trimming filter can be applied independently and the resulting, trimmed read length used in further processing or written to an appropriate file can be the sequence with the shortest length, which should contain only high quality base calls based on the filtering criteria. If the resulting trimmed read length is shorter than the threshold read length, the read can be filtered out entirely.

In an exemplary embodiment, a read filter module may receive an SFF file. The read filter module can store, transmit and/or output trimmed reads and/or a filtered set of reads, and related data and information (for example, for each read, an adapter marker, a sequence key, and/or threshold and quality markers such as per base quality scores, indications of cuts to the reads, and/or the thresholds used in analysis of the data) in SFF or FASTQ file format as well as in a Sequence Alignment/Map ("SAM") file.

Figure 15:
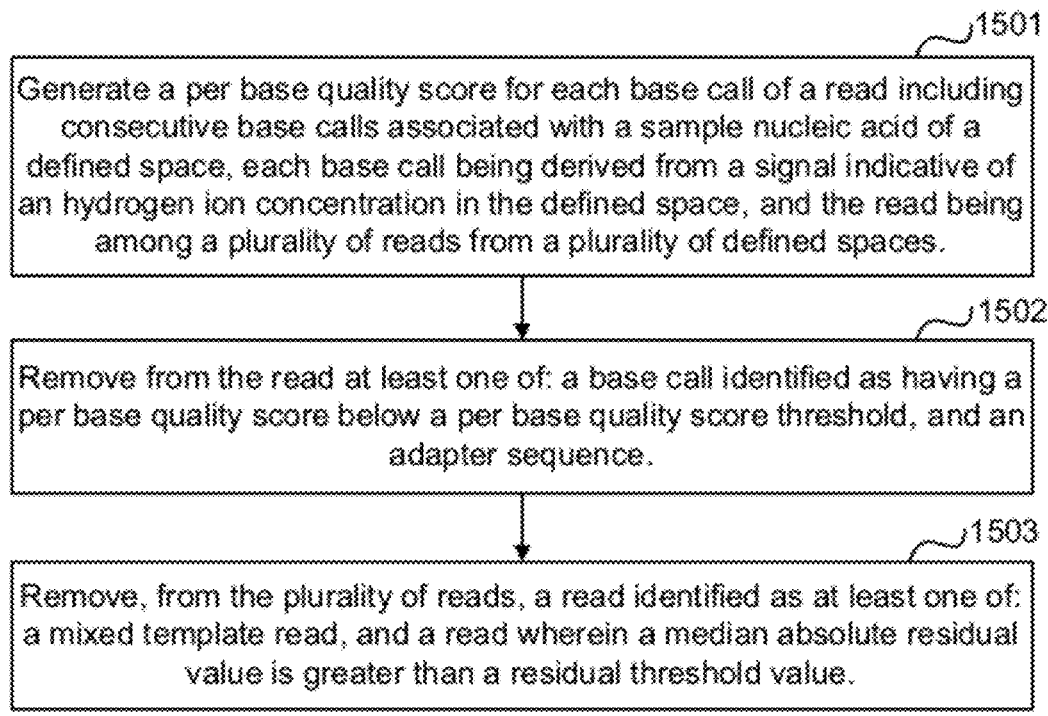
FIG. 15 illustrates a method of nucleic acid sequencing according to an exemplary embodiment.

FIG. 15 illustrates a method of nucleic acid sequencing according to an exemplary embodiment. In step 1501, a module or other hardware and/or software component generates a per base quality score for each base call of a read including consecutive base calls associated with a sample nucleic acid of a defined space, each base call being derived from a signal indicative of an hydrogen ion concentration in the defined space, and the read being among a plurality of reads from a plurality of defined spaces. In step 1502, a module or other hardware and/or software component removes from the read at least one of: (1) a base call identified as having a per base quality score below a per base quality score threshold, and (2) an adapter sequence. In step 1503, a module or other hardware and/or software component removes, from the plurality of reads, a read identified as at least one of: (1) a mixed template read, and (2) a read wherein a median absolute residual value is greater than a residual threshold value.

According to an exemplary embodiment, there is provided a method of nucleic acid sequencing, including: (1) generating a per base quality score for each base call of a read including consecutive base calls associated with a sample nucleic acid of a defined space, each base call being derived from a signal indicative of an hydrogen ion concentration in the defined space, and the read being among a plurality of reads from a plurality of defined spaces; (2) removing from the read at least one of: (a) a base call identified as having a per base quality score below a per base quality score threshold, and (b) an adapter sequence; and (3) removing, from the plurality of reads, a read identified as at least one of: (a) a mixed template read, and (b) a read wherein a median absolute residual value is greater than a residual threshold value. After the removing steps, the remaining and revised reads of the plurality of reads form a filtered set of reads. In such a method, generating a per base quality score may include: calculating at least a first quality predictor value and a second quality predictor value for a base call, the first and second quality predictor values including at least one parameter selected from the group consisting of base position, local noise, read noise, multiple incorporations, phase error, and environment noise; comparing the calculated first quality predictor value and the calculated second quality predictor value to a pre-defined quality metric; and assigning a per base quality score to the base call based on the comparison. The at least one parameter may include a phase error as well as at least one other parameter selected from the group consisting of base position, local noise, read noise, multiple incorporations, and environment noise. In this method, the pre-defined quality metric may include a phred-like table. According to an exemplary embodiment, there is provided a non-transitory machine-readable storage medium comprising instructions which, when executed by a processor, cause the processor to perform such a method of nucleic acid sequencing or related methods and variants thereof.

Figure 16:
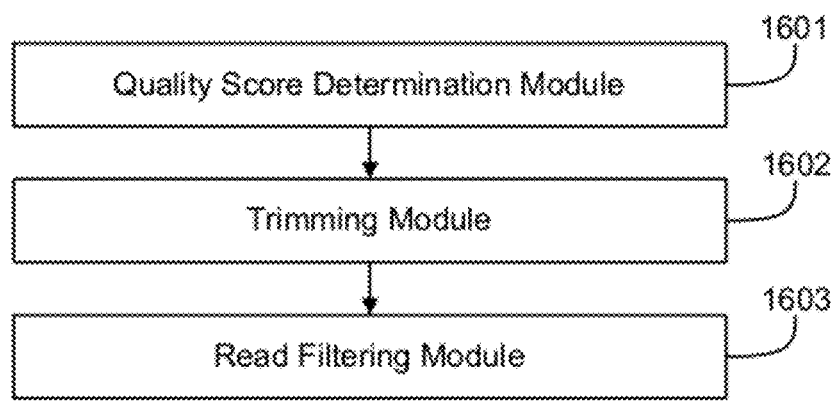
FIG. 16 illustrates components of a read filter module according to an exemplary embodiment.

FIG. 16 illustrates components of a read filter module according to an exemplary embodiment. The read filter module includes a quality score determination module 1601 for determining one or more quality scores for base calls and/or reads, for example; a trimming module 1602 for removing from reads certain base calls having quality scores that fail to reach a minimal threshold and/or certain adapter sequences, for example; and a read filtering module 1603 for removing certain reads, such as mixed template reads and reads failing to meet a certain quality threshold, for example.

According to an exemplary embodiment, there is provided a system for nucleic acid sequencing, including: (1) a per base quality score determination module configured to generate a per base quality score for each base call of a read including consecutive base calls associated with a sample nucleic acid of a defined space and the read is among a plurality of reads from a plurality of defined spaces; (2) a trimming module configured to remove from a read at least one of: (a) a base call identified as having a per base quality score below a per base quality score threshold, and (b) an adapter sequence; and (3) a read filtering module configured to remove, from the plurality of reads, a read identified as at least one of: (a) a mixed template read, and (b) a read wherein a median absolute residual value is greater than a residual threshold value. After any trimming of any base call and adapter sequence by the trimming module and filtering of any mixed template read and read wherein the median absolute residual value is greater than the residual threshold value by the read filtering module, the remaining and revised reads of the plurality of reads form a filtered set of reads.

Figure 17:
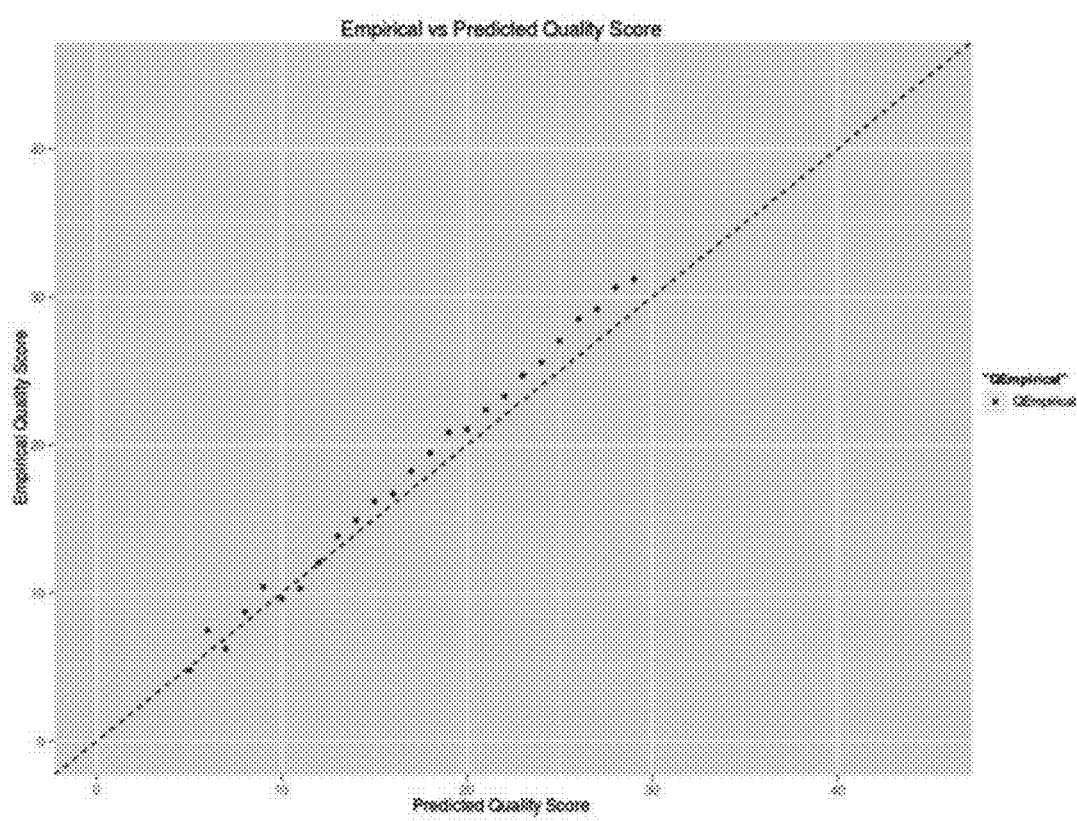
FIG. 17 illustrates a correlation plot showing empirical vs. predicted quality scores according to an exemplary embodiment.

FIG. 17 illustrates a correlation plot showing empirical vs. predicted quality scores according to an exemplary embodiment. The predicted quality scores are based on quality scores derived from probabilities of error using a phred-like quality score. The empirical scores are actual quality score based on reads compared against a known reference. The plot shows a high correlation between predicted and actual quality scores.

Alignment Module

In an exemplary embodiment, an alignment module or aligner may be configured to align reads of a plurality of sample nucleic acids to determine a longer portion of a sample nucleic acid sequence. The alignment module may be based on a TMAP aligner or a BFAST aligner, for example, and may accept as input(s) some or all of the reads, which may include a set of filtered reads received from the read filter module. The alignment module may receive data in SFF file format or FASTQ file format, for example, and it may store, transmit, and/or output one or more sample nucleic acid sequences and related data and information in SAM or BAM file format, for example. The alignment module may also advantageously search, query, and/or use various reference genome and index files to facilitate an alignment and/or as a quality control measure.

In an exemplary embodiment, the alignment module or aligner may further be configured to perform one or more alignment quality control processes, which may include determining whether an identified sample nucleic acid sequence was obtained within an acceptable tolerance limit. The tolerance limit may be defined by the number or percentage of reads that align, and the quality of the alignment may be tested using BFAST, for example.

Figure 18:
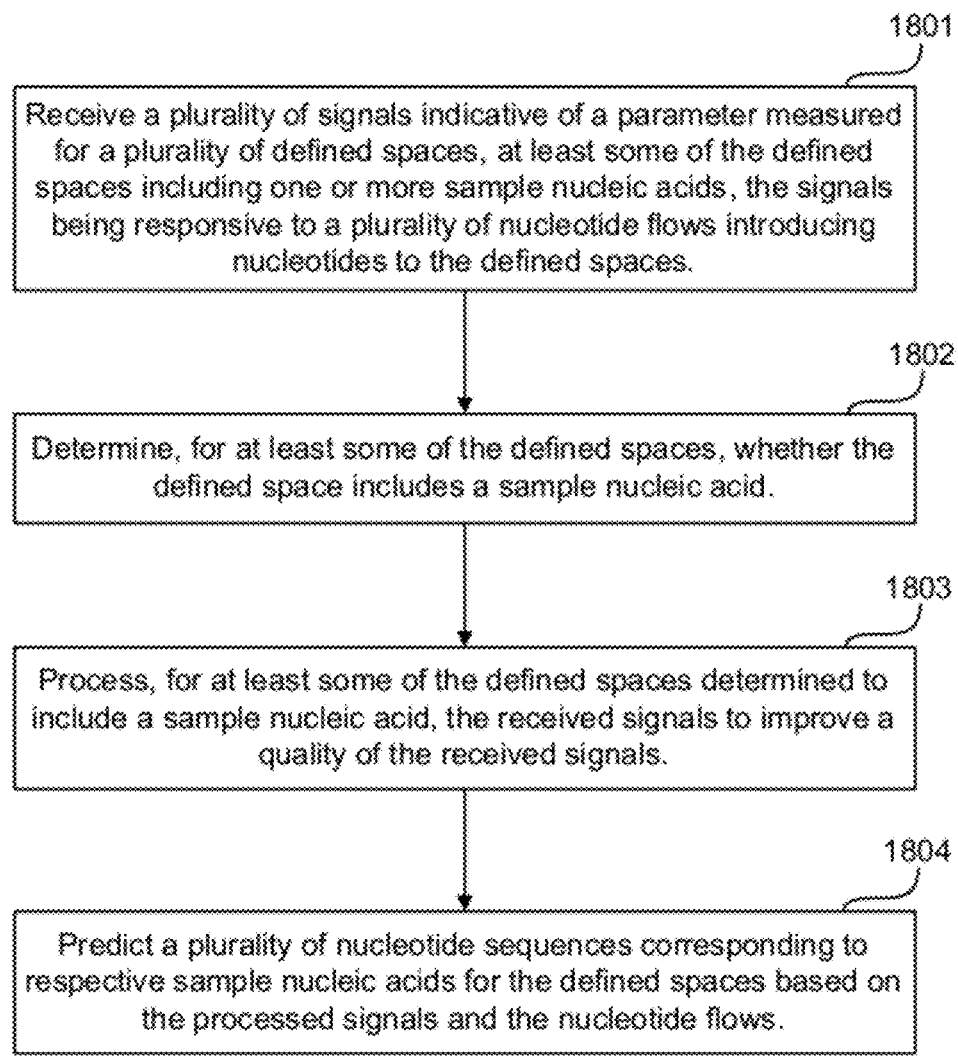
FIG. 18 illustrates a method of nucleic acid sequencing according to an exemplary embodiment.

FIG. 18 illustrates a method of nucleic acid sequencing according to an exemplary embodiment. In step 1801, a module or other hardware and/or software component receives a plurality of signals indicative of a parameter measured for a plurality of defined spaces, at least some of the defined spaces including one or more sample nucleic acids, the signals being responsive to a plurality of nucleotide flows introducing nucleotides to the defined spaces. In step 1802, a module or other hardware and/or software component determines, for at least some of the defined spaces, whether the defined space includes a sample nucleic acid. In step 1803, a module or other hardware and/or software component processes, for at least some of the defined spaces determined to include a sample nucleic acid, the received signals to improve a quality of the received signals. In step 1804, a module or other hardware and/or software component predicts a plurality of nucleotide sequences corresponding to respective sample nucleic acids for the defined spaces based on the processed signals and the nucleotide flows.

Figure 19:
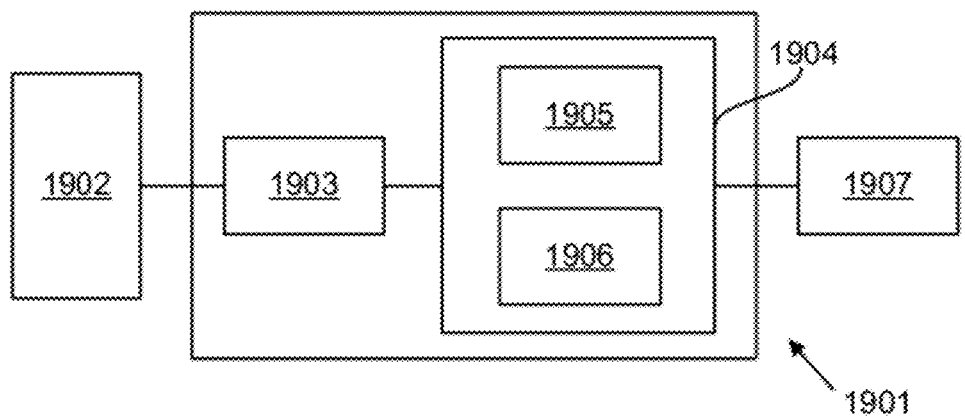
FIG. 19 illustrates a system for nucleic acid sequencing according to an exemplary embodiment.

FIG. 19 illustrates a system 1901 for nucleic acid sequencing according to an exemplary embodiment. The system includes a reactor array 1902; a reader board 1903; a computer and/or server 1904, which includes a CPU 1905 and a memory 1906; and a display 1907, which may be internal and/or external. One or more of these components may be used to perform or implement one or more aspects of the exemplary embodiments described herein.

According to an exemplary embodiment, there is provided a method of nucleic acid sequencing, including: (1) receiving a plurality of signals indicative of a parameter measured for a plurality of defined spaces, at least some of the defined spaces including one or more sample nucleic acids, the signals being responsive to a plurality of nucleotide flows introducing nucleotides to the defined spaces; (2) determining, for at least some of the defined spaces, whether the defined space includes a sample nucleic acid; (3) processing, for at least some of the defined spaces determined to include a sample nucleic acid, the received signals to improve a quality of the received signals; and (4) predicting a plurality of nucleotide sequences corresponding to respective sample nucleic acids for the defined spaces based on the processed signals and the nucleotide flows.

In such a method, in the receiving step, the parameter measured for the defined spaces may include a voltage measurement indicative of hydrogen ion concentration for respective defined spaces. At least some of the defined spaces may include a sample nucleic acid directly or indirectly coupled to a particle. At least some of the defined spaces may include a sample nucleic acid directly or indirectly coupled to a surface of the defined space. The defined spaces may include microwells associated with sensors formed from an integrated circuit chip. The determining step may include evaluating a difference between a first rate of change in an hydrogen ion concentration for the defined space measured for a first solution having a first pH and a second rate of change in the hydrogen ion concentration for the defined space measured for a second solution having a second pH different from the first pH. The determining step may include comparing a rate of change in an hydrogen ion concentration for the defined space measured for a solution having a given pH with a modeled rate of change for the defined space not containing a sample nucleic acid. The determining step may include evaluating, for at least some of the defined spaces determined to include a sample nucleic acid, whether the signals for the defined space are informative or non-informative. The determining step may further include evaluating, for at least some of the defined spaces determined to include a sample nucleic acid and to be informative, whether the defined space includes a library fragment, a test fragment, or an ambiguous fragment. The determining step may further include comparing a flow-space incorporation vector derived from a portion of the signals responsive to a set of initial nucleotide flows for the defined space with at least two pre-defined vectors. The at least two pre-defined vectors may include one or more library fragment flow-space vector. The at least two pre-defined vectors may include one or more test fragment flow-space vector. The at least two pre-defined vectors may include a library fragment flow-space vector that would be expected to result if a pre-defined library fragment key sequence were subjected to the initial nucleotide flows, and a test fragment flow-space vector that would be expected to result if a pre-defined test fragment key sequence were subjected to the initial nucleotide flows. The library fragment flow-space vector and the test fragment flow-space vector may be orthogonal under the set of initial nucleotide flows with respect to at least one, at least two, at least three, or all four of nucleotides A, C, G, and T (as further explained above). The processing step may include modifying the signals to remove noise, the noise being evaluated based at least partly on signals for defined spaces determined not to include a sample nucleic acid. The predicting step may include normalizing the processed signals; estimating, for at least some of the defined spaces determined to include a sample nucleic acid, a number of nucleotide incorporations that occurred in the defined space as a result of each of the nucleotide flows based on the normalized processed signals; and compiling the estimated numbers of nucleotide incorporations for the nucleotide flows into one or more sequences of consecutive base calls for the sample nucleic acid to form one or more reads. The number of nucleotide incorporations may be selected for each of the nucleotide flows from the group consisting of zero, one, two, three, and any other positive integer. The predicting step may further include aligning the one or more reads to predict a sample nucleic acid sequence assembled from the one or more reads for the sample nucleic acids. The predicting step may further include generating a quality metric for the base calls and for the reads; and filtering out from the one or more reads at least one of: any read that contains at least a threshold number of base calls failing to meet a minimal threshold of base call quality, and any read that fails to meet a minimal threshold of read quality. The predicting step may further include generating a quality score for at least some of the base calls forming at least a portion of the one or more reads. The generating step may include calculating at least a first quality predictor value and a second quality predictor value for each base call, the first and second quality predictor values including at least one parameter selected from the group consisting of base position, local noise, read noise, multiple incorporations, phase error, and environment noise; comparing the calculated first quality predictor value and the calculated second quality predictor value to a pre-defined quality metric; and assigning a quality score to the at least some of the base calls based upon the comparison. The at least one parameter may include a phase error as well as at least one other parameter selected from the group consisting of base position, local noise, read noise, multiple incorporations, and environment noise. The predicting step may include removing from the at least some of the base calls forming at least a portion of the one or more reads at least one of: any base call identified as having a quality score below a quality score threshold, and an adapter sequence;

and filtering out from the at least a portion of the one or more reads at least one of: any read identified as a mixed template read, and any read identified as having a median absolute residual value greater than a residual threshold value, thereby generating a filtered set of reads. The predicting step may further include aligning the filtered set of reads to predict a sample nucleic acid sequence assembled from the filtered set of reads for the sample nucleic acids. The method may include transmitting, displaying, storing, printing or outputting to a user interface device, a computer readable storage medium, a local computer system or a remote computer system, information related to the predicted nucleotide sequences of the sample nucleic acids or other parameters, predictions, data or signals generated or used by the method.

According to an exemplary embodiment, there is provided a non-transitory machine-readable storage medium comprising instructions which, when executed by a processor, cause the processor to perform such a method for nucleic acid sequencing or related methods and variants thereof. According to an exemplary embodiment, there is provided a system, including: a machine-readable memory; and a processor configured to execute machine-readable instructions, which, when executed by the processor, cause the system to perform such a method for nucleic acid sequencing or related methods and variants thereof.

Figure 20:
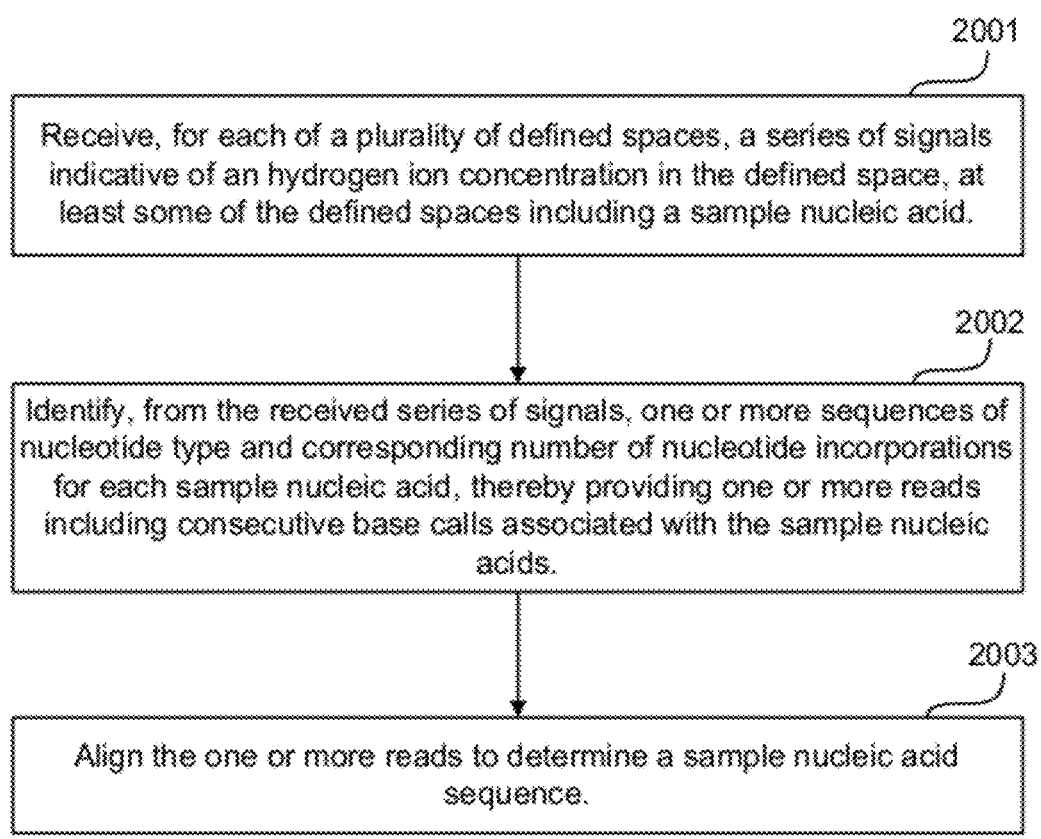
FIG. 20 illustrates a method of nucleic acid sequencing according to an exemplary embodiment.

FIG. 20 illustrates a method of nucleic acid sequencing according to an exemplary embodiment. In step 2001, a module or other hardware and/or software component receives, for each of a plurality of defined spaces, a series of signals indicative of an hydrogen ion concentration in the defined space, at least some of the defined spaces including a sample nucleic acid. In step 2002, a module or other hardware and/or software component identifies, from the received series of signals, one or more sequences of nucleotide type and corresponding number of nucleotide incorporations for each sample nucleic acid, thereby providing one or more reads including consecutive base calls associated with the sample nucleic acids. In step 2003, a module or other hardware and/or software component may align the one or more reads to determine a sample nucleic acid sequence.

According to an exemplary embodiment, there is provided a method of nucleic acid sequencing, including: (1) receiving, for each of a plurality of defined spaces, a series of signals indicative of an hydrogen ion concentration in the defined space, at least some of the defined spaces including a sample nucleic acid; (2) identifying, from the received series of signals, one or more sequences of nucleotide type and corresponding number of nucleotide incorporations for each sample nucleic acid, thereby providing one or more reads including consecutive base calls associated with the sample nucleic acids; and (3) aligning the one or more reads to determine a sample nucleic acid sequence. In such a method, in the receiving step, the signals may include voltage measurements indicative of the hydrogen ion concentration in the defined space. At least some of the defined spaces may include a sample nucleic acid directly or indirectly coupled to a particle. At least some of the defined spaces may include a sample nucleic acid directly or indirectly coupled to a surface of the defined space. The defined spaces may include microwells associated with sensors formed from an integrated circuit chip. According to an exemplary embodiment, there is provided a non-transitory machine-readable storage medium comprising instructions which, when executed by a processor, cause the processor to perform such a method for nucleic acid sequencing or related methods and variants thereof.

According to an exemplary embodiment, there is provided a system, including: (1) a data processing module configured to receive a series of signals characteristic of an hydrogen ion concentration associated with reaction confinement regions or defined spaces associated with at least one sample nucleic acid; and (2) a classification module configured to determine a presence or absence of a sample-containing particle in the reaction confinement regions or defined spaces. The system may further include a signal processing module configured to analyze data and/or signals derived from the reaction confinement regions or defined spaces determined to contain a sample-containing particle, and to output signals indicative of nucleotide incorporation events or non-events. The system may further include a base caller module configured to transform the output signals into base calls and compile consecutive base calls for the at least one sample nucleic acid into at least one read including a plurality of sequential or consecutive base calls associated with the at least one sample nucleic acid. The system may further include a read filter module configured to generate a quality metric for each base call and for each read to facilitate filtering out of low quality reads. The system may further include an alignment module configured to align the reads of a plurality of sample nucleic acids to determine a sample nucleic acid sequence. The system may further include a data output module configured to transmit, display, store, print or output to a user interface device, a computer readable storage medium, a local computer system or a remote computer system, information related to the determined nucleotide sequence or other parameters, predictions, data or signals generated or used by the system.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various additional exemplary embodiments may be derived by repeating, adding, or substituting any generically or specifically described features and/or components and/or substances and/or steps and/or operating conditions set forth in one or more of the above-described exemplary embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed exemplary embodiments may be considered to be a potential optional feature, component, aspect, step, or other characteristic of any other of the above-discussed exemplary embodiments so long as the objective of such any other of the above-discussed exemplary embodiments remains achievable, unless specifically stated otherwise.

Although the present description described in detail certain exemplary embodiments, other embodiments are also possible and within the scope of the present invention. Variations and modifications will be apparent to those skilled in the art from consideration of the specification and figures and practice of the teachings described in the specification and figures, and the claims.

The invention claimed is:

1. A method for nucleic acid sequencing, comprising:
for each of a plurality of defined spaces of a chip, a template, or a substrate, wherein each defined space is in communication with a respective sensor, and wherein at least some of the defined spaces comprise one or more sample nucleic acids, receiving at a processor, from the respective sensor of each defined space, a signal comprising a voltage measurement indicative of a hydrogen ion concentration, wherein the signal is in response to exposure of the corresponding defined space to a first hydrogen ion concentration associated with a first buffer or a first reagent, and then exposure of the corresponding defined space to a second hydrogen ion concentration associated with a second buffer or a second reagent;
first determining, for at least some of the defined spaces of the plurality of defined spaces, time delays in the signals, wherein the time delays are associated with diffusions resulting from the exposure of the defined spaces to the first hydrogen ion concentration and then the exposure to the second hydrogen ion concentration;
second determining whether the defined space comprises a sample nucleic acid or does not comprise a sample nucleic acid based on the determined time delays;
based on the second determining step, classifying into a first group the defined spaces that comprise a sample nucleic acid and a second group the defined spaces that do not comprise a sample nucleic acid;
receiving, at the processor, a second signal from the sensor of each defined space, wherein the second signal is responsive to a nucleotide flow introducing a nucleotide to the defined space for a plurality of nucleotide flows;
subtracting a noise component from the second signal for a respective defined space in the first group to form a noise-reduced signal, wherein the noise component is based on an average of one or more second signals corresponding to one or more defined spaces in the second group; and
predicting a plurality of nucleotide sequences corresponding to the sample nucleic acids for respective defined spaces in the first group, the predicting including estimating a number of nucleotide incorporations in response to the nucleotide flow based on the noise-reduced signal for each nucleotide flow in the plurality of nucleotide flows.

2. The method of claim 1, wherein the second determining step, the defined space is determined to comprise a sample nucleic acid when the determined time delay is longer than the time delay determined from one or more neighboring defined spaces.

3. The method of claim 1, wherein at least some of the defined spaces comprise a sample nucleic acid directly or indirectly coupled to a particle.

4. The method of claim 1, wherein at least some of the defined spaces comprise a sample nucleic acid directly or indirectly coupled to a surface of the defined space.

5. The method of claim 1, wherein the defined spaces comprise microwells in communication with the sensors in an integrated circuit chip.

6. The method of claim 1, wherein the time delay of the signal spans a change in a hydrogen ion concentration in the defined space from the first hydrogen ion concentration to the second hydrogen ion concentration.

7. The method of claim 1, wherein the second determining step comprises comparing a rate of change in a hydrogen ion concentration for the defined space with a modeled rate of change associated with an absence of a sample nucleic acid.

8. The method of claim 1, further comprising, evaluating, for at least some of the defined spaces of the first group, whether the signals for the defined space are informative or non-informative, wherein a non-informative designation indicates that the defined space is not functional.

9. The method of claim 8, further comprising evaluating, for at least some of the defined spaces of the first group evaluated to be informative, whether the defined space comprises a library fragment, a test fragment, or an ambiguous fragment.

10. The method of claim 1, further comprising:
determining a flow-space vector derived from a series of initial signals in response to a set of initial nucleotide flows for at least one defined space, wherein the flow-space vector indicates an incorporation event or a non-incorporation for each nucleotide in the set of initial nucleotide flows; and
comparing the flow-space vector with at least two pre-defined vectors.

11. The method of claim 10, wherein the at least two pre-defined vectors comprise:
a library fragment flow-space vector that would be expected to result if a predefined library fragment key sequence were subjected to the initial nucleotide flows; and
a test fragment flow-space vector that would be expected to result if a pre-defined test fragment key sequence were subjected to the initial nucleotide flows.

12. The method of claim 11, wherein the library fragment flow-space vector and the test fragment flow-space vector are orthogonal under the set of initial nucleotide flows with respect to at least two nucleotides selected from nucleotides A, C, G, and T.

13. The method of claim 11, wherein the library fragment flow-space vector and the test fragment flow-space vector are orthogonal under the set of initial nucleotide flows with respect to at least three nucleotides selected from nucleotides A, C, G, and T.

14. The method of claim 1, wherein the predicting step comprises:
compiling the estimated numbers of nucleotide incorporations corresponding to each of the plurality of nucleotide flows into one or more sequences of consecutive base calls for the sample nucleic acid to form one or more reads.

15. The method of claim 14, wherein the number of nucleotide incorporations is selected for each nucleotide from the group consisting of zero, one, two, and any other positive integer.

16. The method of claim 14, wherein the predicting step comprises:
generating a quality metric for the base calls and for the reads; and
filtering out from the one or more reads at least one of:
any read that contains at least a threshold number of base calls failing to meet a minimal threshold of base call quality, and
any read that fails to meet a minimal threshold of read quality.

17. The method of claim 14, wherein the predicting step comprises:
calculating at least a first quality predictor value and a second quality predictor value for a given base call, the first and second quality predictor values including a phase error and at least one other parameter selected from the group consisting of base position, local noise, read noise, multiple incorporations, and environment noise, wherein a phase error quality predictor indicates a number of incorporations of a same nucleotide in a previous nucleotide flow, wherein a base position quality predictor indicates a position of the given base in the read from the start of the nucleic acid sequence, wherein a local noise quality predictor indicates noise in a first vicinity of the given base in the nucleic acid sequence, wherein a read noise quality predictor is based on a mean and a standard deviation of 0-mers and 1-mers of the read, wherein a multiple incorporations quality predictor for multiple incorporations of the same nucleotide in a particular nucleotide flow, indicating a homopolymer region, assigns to a last base in the homopolymer region a value based on a total number of incorporations during the particular nucleotide flow and assigns a value of 1 to other bases in the homopolymer region, and wherein an environment noise quality predictor indicates noise in a second vicinity of the given base in the nucleic acid sequence, where the first vicinity spans fewer bases than the second vicinity;
comparing the calculated first quality predictor value and the calculated second quality predictor value to corresponding pre-defined quality metrics of a look-up table, wherein the look-up table includes rows of pre-defined quality metrics and a quality score associated with each row;
selecting the row of the look-up table where the first and second quality predictor values are less than the corresponding pre-defined quality metrics in the selected row; and
assigning the quality score associated with the selected row to the given base call.

18. The method of claim 17, wherein the predicting step comprises:
removing from the at least some of the base calls forming at least a portion of the one or more reads at least one of:
any base call identified as having a quality score below a quality score threshold, and
an adapter sequence; and
filtering out from the at least a portion of the one or more reads at least one of:
any read identified as a mixed template read, and
any read identified as having a median absolute residual value greater than a residual threshold value, thereby generating a filtered set of reads.

19. The method of claim 18, wherein the predicting step comprises aligning the filtered set of reads to predict a sample nucleic acid sequence assembled from the filtered set of reads for the sample nucleic acids.

20. The method of claim 14, wherein the predicting step comprises aligning the one or more reads to predict a sample nucleic acid sequence assembled from the one or more reads for the sample nucleic acids.

21. The method of claim 1, comprising transmitting, displaying, storing, printing or outputting to a user interface device, a computer readable storage medium, a local computer system or a remote computer system, information related to the predicted nucleotide sequences of the sample nucleic acids or other parameters, predictions, or data generated or used by the method.

22. A non-transitory machine-readable storage medium comprising instructions which, when executed by a processor, cause the processor to perform a method for nucleic acid sequencing comprising:
for each of a plurality of defined spaces of a chip, a template, or a substrate, wherein each defined space is in communication with a respective sensor, and wherein at least some of the defined spaces comprise one or more sample nucleic acids, receiving, from the respective sensor of each defined space, a signal comprising a voltage measurement indicative of a hydrogen ion concentration, wherein the signal is in response to exposure of the corresponding defined space to a first hydrogen ion concentration associated with a first buffer or a first reagent, and then exposure of the corresponding defined space to a second hydrogen ion concentration associated with a second buffer or a second reagent;
first determining, for at least some of the defined spaces of the plurality of defined spaces, time delays in the signals, wherein the time delays are associated with diffusions resulting from the exposure of the defined spaces to the first hydrogen ion concentration and then the exposure to the second hydrogen ion concentration;
second determining whether the defined space comprises a sample nucleic acid or does not comprise a sample nucleic acid based on the determined time delays;
based on the second determining step, classifying into a first group the defined spaces that comprise a sample nucleic acid and a second group the defined spaces that do not comprise a sample nucleic acid;
receiving, at the processor, a second signal from the sensor of each defined space, wherein the second signal is responsive to a nucleotide flow introducing a nucleotide to the defined space for a plurality of nucleotide flows;

subtracting a noise component from the second signal for a respective defined space in the first group to form a noise-reduced signal, wherein the noise component is based on an average of one or more second signals corresponding to one or more defined spaces in the second group; and predicting a plurality of nucleotide sequences corresponding to the sample nucleic acids for respective defined spaces in the first group, the predicting including estimating a number of nucleotide incorporations in response to the nucleotide flow based on the noise-reduced signal for each nucleotide flow in the plurality of nucleotide flows.

23. The non-transitory machine-readable storage medium of claim 22, wherein the predicting step comprises:
compiling the estimated numbers of nucleotide incorporations corresponding to each of the plurality of nucleotide flows into one or more sequences of consecutive base calls for the sample nucleic acid to form one or more reads.

24. The non-transitory machine-readable storage medium of claim 23, wherein the predicting step comprises:
generating a quality metric for the base calls and for the reads; and
filtering out from the one or more reads at least one of:
any read that contains at least a threshold number of base calls failing to meet a minimal threshold of base call quality, and
any read that fails to meet a minimal threshold of read quality.

25. The non-transitory machine-readable storage medium of claim 23, wherein the predicting step comprises:
calculating at least a first quality predictor value and a second quality predictor value for a given base call, the first and second quality predictor values including a phase error and at least one other parameter selected from the group consisting of base position, local noise, read noise, multiple incorporations, and environment noise, wherein a phase error quality predictor indicates a number of incorporations of a same nucleotide in a previous nucleotide flow, wherein a base position quality predictor indicates a position of the given base in the read from the start of the nucleic acid sequence, wherein a local noise quality predictor indicates noise in a first vicinity of the given base in the nucleic acid sequence, wherein a read noise quality predictor is based on a mean and a standard deviation of 0-mers and 1-mers of the read, wherein a multiple incorporations quality predictor for multiple incorporations of the same nucleotide in a particular nucleotide flow, indicating a homopolymer region, assigns to a last base in the homopolymer region a value based on a total number of incorporations during the particular nucleotide flow and assigns a value of 1 to other bases in the homopolymer region, and wherein an environment noise quality predictor indicates noise in a second vicinity of the given base in the nucleic acid sequence, where the first vicinity spans fewer bases than the second vicinity;
comparing the calculated first quality predictor value and the calculated second quality predictor value to corresponding pre-defined quality metrics of a look-up table, wherein the look-up table includes rows of pre-defined quality metrics and a quality score associated with each row;
selecting the row of the look-up table where the first and second quality predictor values are less than the corresponding pre-defined quality metrics in the selected row; and
assigning the quality score associated with the selected row to the given base call.

26. The non-transitory machine-readable storage medium of claim 24, wherein the predicting step comprises:
removing from the at least some of the base calls forming at least a portion of the one or more reads at least one of:
any base call identified as having a quality score below a quality score threshold, and
an adapter sequence; and
filtering out from the at least a portion of the one or more reads at least one of:
any read identified as a mixed template read, and
any read identified as having a median absolute residual value greater than a residual threshold value, thereby generating a filtered set of reads.

27. The non-transitory machine-readable storage medium of claim 26, wherein the predicting step comprises aligning the filtered set of reads to predict a sample nucleic acid sequence assembled from the filtered set of reads for the sample nucleic acids.

28. A system, comprising:
a machine-readable memory; and
a processor configured to execute machine-readable instructions, which, when executed by the processor, cause the system to perform steps including:
for each of a plurality of defined spaces of a chip, a template, or a substrate, wherein each defined space is in communication with a respective sensor, and wherein at least some of the defined spaces comprise one or more sample nucleic acids, receiving, from the respective sensor of each defined space, a signal comprising a voltage measurement indicative of a hydrogen ion concentration, wherein the signal is in response to exposure of the corresponding defined space to a first hydrogen ion concentration associated with a first buffer or a first reagent, and then exposure of the corresponding defined space to a second hydrogen ion concentration associated with a second buffer or a second reagent;
first determining, for at least some of the defined spaces of the plurality of defined spaces, time delays in the signals, wherein the time delays are associated with diffusions resulting from the exposure of the defined spaces to the first hydrogen ion concentration and then the exposure to the second hydrogen ion concentration;
second determining whether the defined space comprises a sample nucleic acid or does not comprise a sample nucleic acid based on the determined time delays;
based on the second determining step, classifying into a first group the defined spaces that comprise a sample nucleic acid and a second group the defined spaces that do not comprise a sample nucleic acid;
receiving, at the processor, a second signal from the sensor of each defined space, wherein the second signal is responsive to a nucleotide flow introducing a nucleotide to the defined space for a plurality of nucleotide flows;
subtracting a noise component from the second signal for a respective defined space in the first group to form a noise-reduced signal, wherein the noise component is based on an average of one or more second signals corresponding to one or more defined spaces in the second group; and predicting a plurality of nucleotide sequences corresponding to the sample nucleic acids for respective defined spaces in the first group, the predicting including estimating a number of nucleotide incorporations in response to the nucleotide flow based on the noise-reduced signal for each nucleotide flow in the plurality of nucleotide flows.

* * * * *

SEQUENCE LISTING

<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: Exemplary Strand

<400> SEQUENCE: 1
agtcaagcgt cccatg         16